US005762798A

United States Patent [19]
Wenthold et al.

[11] Patent Number: 5,762,798
[45] Date of Patent: Jun. 9, 1998

[54] HOLLOW FIBER MEMBRANES AND METHOD OF MANUFACTURE

[75] Inventors: Randal M. Wenthold, Belle Plaine; Robert T. Hall, II. Welch; Robert G. Andrus, Minneapolis; Paul D. Brinda, Robbinsdale; Louis C. Cosentino, Deephaven; Robert F. Reggin, Annandale; Daniel T. Pigott, Minnetonka, all of Minn.

[73] Assignee: Minntech Corporation, Minneapolis, Minn.

[21] Appl. No.: 58,904

[22] Filed: May 6, 1993

Related U.S. Application Data

[63] Continuation-in-part of Ser. No. 684,585, Apr. 12, 1991, abandoned, Ser. No. 902,389, Jun. 23, 1992, abandoned, and Ser. No. 958,027, Oct. 7, 1992, abandoned.

[51] Int. Cl.$^6$ .................................................. B01D 69/08
[52] U.S. Cl. .................. 210/500.23; 96/10; 210/500.41; 210/500.42; 264/171.26; 264/178 F
[58] Field of Search ................. 210/500.23, 500.41, 210/651, 654, 652, 321.89, 500.43; 264/41, 49, 178 F; 96/8, 10

[56] References Cited

U.S. PATENT DOCUMENTS

| 3,180,845 | 4/1965 | Knudsen . |
| 3,423,491 | 1/1969 | McLain et al. . |
| 3,526,588 | 9/1970 | Michaels et al. . |

(List continued on next page.)

FOREIGN PATENT DOCUMENTS

| 0082433 | 6/1983 | European Pat. Off. . |
| 2482468 | 11/1981 | France . |
| 2829630 | 1/1974 | Germany . |
| 2651818 | 6/1977 | Germany . |
| 3018667 | 11/1981 | Germany . |
| 3149976 | 6/1983 | Germany . |
| 8702924 | 12/1987 | Netherlands . |

OTHER PUBLICATIONS

English Abstract of Japanesee Reference 55–106,243 (Published Aug. 1980).

Cabasso et al "Polysulfone Hollow Fibers. I. Spinning and Properties". *Journal of Applied Polymer Science*, 20:2377–2394 (1976).

Cabasso et al "Polysulfone Hollow Fibers. II. Morphology", *Journal of Applied Polymer Science*, 21:165–180 (1977).

Cabasso et al. "Porosity and Pore Size Determination in Polysulfone Hollow Fibers", *Journal of Applied Polymer Science*, 21:1883–1900 (1977).

Cabasso, "Hollow Fiber Membranes". *Kirk–Othmer Encyclopedia & Chemical Technology*, 3rd edition, John Wiley & Sons (editor: Martin Grayson). 12:492–517 (1984).

Wijmans et al., "The Mechanism of Formation of Microporous or Skinned Membranes Produced by Immersion Precipitation". *Journal of Membrane Science*, 14:263–274 (1983).

Edward F. Leonard, "Dialysis", *Kirk–Othmer Encyclopedia of Chemical Technology*, 3rd edition, John Wiley & Sons (editor: Martin Grayson), 7:564–579 (1984).

(List continued on next page.)

*Primary Examiner*—Joseph W. Drodge
*Attorney, Agent, or Firm*—Barbara A. Wrigley

[57] ABSTRACT

An asymmetrical, microporous, hollow fiber membrane is made from a polymeric dope mixture of polysulfone and polyvinyl pyrrolidone dissolved in an aprotic solvent. The physical morphology of the hollow fiber membrane, i.e., the asymmetric microporous wall, is rapidly formed by passing the polymeric dope mixture through an outer annular orifice of a tube-in-orifice spinneret while simultaneously passing a precipitating solution through the central tube of the spinneret. The emerging hollow fiber travels substantially downward for about 0.01–10 m before submersion into a quenching bath. The asymmetrical, microporous, hollow fiber membrane is biocompatible and suitable for use in, for example, dialysis, hemodialysis, ultrafiltration, and water filtration applications.

90 Claims, 6 Drawing Sheets

U.S. PATENT DOCUMENTS

| | | |
|---|---|---|
| 3,615,024 | 10/1971 | Michaels . |
| 3,691,068 | 9/1972 | Cross . |
| 3,708,458 | 1/1973 | Alberino et al. . |
| 3,763,055 | 10/1973 | White et al. . |
| 3,775,308 | 11/1973 | Yasuda . |
| 3,948,823 | 4/1976 | Lee et al. . |
| 4,026,977 | 5/1977 | Bourganel . |
| 4,046,843 | 9/1977 | Sano et al. ............... 210/500.42 X |
| 4,051,300 | 9/1977 | Klein et al. . |
| 4,100,238 | 7/1978 | Shinomura . |
| 4,113,628 | 9/1978 | Alegranti . |
| 4,115,492 | 9/1978 | Mahoney et al. . |
| 4,203,847 | 5/1980 | Grandine, 2nd . |
| 4,207,182 | 6/1980 | Marze . |
| 4,208,508 | 6/1980 | Hashino et al. . |
| 4,229,291 | 10/1980 | Walch et al. . |
| 4,230,583 | 10/1980 | Chiolle et al. . |
| 4,286,015 | 8/1981 | Yoshida et al. . |
| 4,342,711 | 8/1982 | Joh et al. . |
| 4,351,860 | 9/1982 | Yoshida et al. . |
| 4,432,875 | 2/1984 | Wrasidlo et al. . |
| 4,444,663 | 4/1984 | Aoyagi et al. . |
| 4,532,041 | 7/1985 | Shuey et al. . |
| 4,545,910 | 10/1985 | Marze . |
| 4,655,840 | 4/1987 | Wittwer et al. . |
| 4,664,859 | 5/1987 | Knoop . |
| 4,714,481 | 12/1987 | Matsura et al. . |
| 4,720,342 | 1/1988 | Takemura et al. . |
| 4,720,343 | 1/1988 | Walch et al. . |
| 4,722,795 | 2/1988 | Gohl et al. . |
| 4,746,474 | 5/1988 | Kohn . |
| 4,772,391 | 9/1988 | Baker . |
| 4,798,847 | 1/1989 | Roesink et al. . |
| 4,826,599 | 5/1989 | Bikson et al. ............... 264/178 F |
| 4,853,127 | 8/1989 | Le et al. . |
| 4,882,223 | 11/1989 | Aptel et al. ............... 210/500.23 X |
| 4,895,657 | 1/1990 | Polaschegg . |
| 4,900,449 | 2/1990 | Kraus et al. . |
| 4,900,502 | 2/1990 | Babcock et al. . |
| 4,906,375 | 3/1990 | Heilmann . |
| 4,923,598 | 5/1990 | Schal . |
| 4,933,083 | 6/1990 | Jones, Jr. . |
| 4,963,303 | 10/1990 | Anderson . |
| 4,964,990 | 10/1990 | Kraus et al. . |
| 4,983,191 | 1/1991 | Ekiner et al. . |
| 5,009,824 | 4/1991 | Walch et al. . |
| 5,015,270 | 5/1991 | Ekiner et al. . |
| 5,035,802 | 7/1991 | Yamasaki et al. . |
| 5,049,276 | 9/1991 | Sasaki ............... 210/500.23 |
| 5,067,970 | 11/1991 | Wang et al. . |
| 5,076,925 | 12/1991 | Roesink et al. . |
| 5,085,676 | 2/1992 | Ekiner et al. . |
| 5,151,227 | 9/1992 | Nguyen et al. . |
| 5,160,672 | 11/1992 | Sasaki et al. . |
| 5,163,977 | 11/1992 | Jensvold et al. . |
| 5,181,940 | 1/1993 | Bikson et al. ............... 96/10 |
| 5,480,554 | 1/1996 | Degen et al. ............... 210/500.41 X |

OTHER PUBLICATIONS

*Processing of Thermoplastic Material*, (editor: Ernest C. Bernhardt) Reinhold, New York, pp. 582,584,600,602,616, 628,630,632,634 (1959).

Pusch and Walch, "Synthetic Membranes: State of the Art", *Desalination*, 35: 5 –20 (1980).

Uragami et al., "Studies on Synthesis and Pereability of Special Polymer Membranes", *Polymer–Bulletin*, 4:617–622 (Spring 1981).

Japanese Publication 63–277251 (Published Nov. 15, 1988).

V. Chen et al., "The use of anionic surfactants for reducing fouling of ultrafiltration membranses: their effects and optimization," *Journel of Membrane Science*, vol. 67, Nos. 2/3, 20, Mar. 1992.

Japanese Publication 60064602 (Published Aug. 13, 1985).

Japanese Publication 61101208 (Published 6110208 (Published Sep. 24, 1986).

Japanese Publication 58014913 (Published Apr. 9, 1983).

European Patent Search Report Dated Feb. 17, 1994 (Corresponding to US Serial No: 08/058940).

PCT Search Report dated Aug. 18, 1993 (Corresponding to US Serial No.: 08/058904).

HOLLOW FIBER MEMBRANES AND METHOD OF MANUFACTURE

This application is a continuation-in-part of applications Ser. No. 07/684,585 filed Apr. 12, 1991, Ser. No. 07/902,389 filed Jun. 23, 1992 and Ser. No. 07/958,027 filed Oct. 7, 1992 all now abandoned the entireties of which are hereby incorporated by reference.

BACKGROUND OF THE INVENTION

1. Field of the Invention

The invention relates to improved hollow fiber membranes and an improved process for the production of those membranes. In particular, the invention relates to improved asymmetrical microporous hollow fibers incorporating a polysulfone, a polysulfone with a low molecular weight surfactant or a polyimide. The asymmetrical, microporous hollow fibers incorporating a low weight surfactant have improved flux and rewetting characteristics. The asymmetrical, microporous hollow fibers incorporating a polyimide have low water or blood leachable impurities.

The unique process for the production of these membranes involves passing a polymeric solution through an outer annulus of die to create an annular stream and a precipitating fluid through the inner orifice of the die creating a stream within the annular stream resulting in hollow fiber formation.

2. Description of the Related Art.

A microporous, hollow fiber is a polymeric capillary tube having an outside diameter of less than or equal to 1 mm, and whose wall functions as a semipermeable membrane. The fibers are useful in separation processes involving transport mainly through sorption and diffusion. Such processes include dialysis, hemodialysis, ultrafiltration, hemofiltration, plasma filtration, blood separation drug release in artificial organs and water filtration where ultra-pure water is needed such as in the electronic and pharmaceutical industries. Each of these applications have various requirements including pore size, strength, biocompatibility, cost and speed of production and reproducibility.

Given the varying uses to which this fiber may be applied, it is highly desirable that the hollow fiber membrane have as little leachable impurities as possible in water, blood, from 0% to saturated solutions of NaCl in water, and other similar type of aqueous solutions. For certain applications, it may also be desired that the membranes be easily or immediately wettable by water, blood and other types of aqueous solutions without the need for costly polymer additives, post fiber-formation treatments with wetting agents or both. In other applications, it would be highly desirable for these membranes to remove endotoxin from the solution to be filtered. In still other applications, it may be desirable to be able to repeatedly autoclaved without the loss of the rewetting characteristic.

Early hollow fibers have included regenerated cellulose material and modified polyacrylonitrile material. However, it is difficult to control the porosity and pore size of these fibers, and for some applications, composite membranes consisting of an ultra-thin layer contiguous with a more porous substrate are needed to provide the necessary strength.

Early hollow fiber membranes have also been prepared from hydrophobic polymers such as polysulfones, aromatic polyamides and polyimides, and polyamide-imides. However, the hydrophobic nature of these polymer presents difficulties with wetting these membranes when used in aqueous systems. Therefore, hydrophilic polymers such as polyvinyl alcohol, polyvinyl acetate co-polymers, polyvinylpyrrolidone and polyvinylpyrrolidine have typically been incorporated directly into the fibers to achieve a hydrophilic fiber that wets easily. Alternatively, polyethylene glycol, glycerol and/or a variety of surfactants have been incorporated directly into the fibers or used post-fiber formation to achieve wettability.

In an attempt to overcome the difficulties and limitations of the prior art, Klein et al., U.S. Pat. No. 4,051,300 discloses a process for the preparation of hollow microporous fibers capable of withstanding from 600 psi to 2000 psi applied pressure without collapse. The fibers are prepared by a solution spinning process. This process comprises extruding a polymer solution of a first fiber forming polymer and a second, hydrophilic polymer through the outer annulus of a coextrusion die, providing a precipitating liquid miscible with the polymer solvent through an inner or center orifice in the coextrusion die. The precipitating liquid forms an inner liquid core surrounded by the polymer solution. The precipitation liquid causes the annular polymer solution to precipitate into a hollow fiber. In further processing, the fiber is washed free of the residual solvents and nonsolvents.

The polymer solution generally comprises about 15–65 combined weight-% of a first, fiber forming polymer and a second polymer. Fiber forming polymers disclosed include polysulfone and polyaromatic polyamide polymers. Polymers disclosed for use as the second polymer are polyvinylpyrrolidone polymers. The solvent for the polymer solution disclosed in the examples of the patent is dimethylacetamide (DMA) and dimethylformamide (DMF). Precipitating liquid disclosed in Klein include water/DMA, air and water/isopropyl alcohol. The fibers prepared by the process of Klein are designed only to be used as the support structure of a final composite membrane. The actual selective membrane is applied as an ultrathin coating to this support structure in an additional step or steps. Further, this process is a relatively slow, time consuming step wherein fiber is produced at a rate of about 20 m/min.

The limitations on speed of hollow fiber production, in processes similar to Klein are reinforced in the teachings of Joh et al., U.S. Pat. No. 4,342,711. This patent is drawn to a process for forming hollow fibers. An object of the invention is to allow the rapid manufacture of these fibers. However, Joh discloses that manufacturing process which allow the rapid diffusion of the core liquid or precipitating solution into the fiber-forming outer solution are limited to low process speeds, e.g., about 5–15 m/min.

This limitation is borne out in another patent drawn to a method for making fibers for hemodialysis, Heilmann, U.S. Pat. No. 4,906,375. This patent discloses a process comprising wet spinning a polymer solution made up of a solvent, about 12 to 20 wt. % of a first, hydrophobic polymer and 2–10 wt. % of a hydrophilic polyvinylpyrrolidone polymer and simultaneously passing through a hollow internal core a precipitant solution comprising an aprotic solvent in conjunction with at least 25 wt. % non-solvent. Hydrophobic polymers disclosed include polysulfones such as a polyether sulfone, polycarbonates, and polyamides. The polar aprotic solvents disclosed include dimethylformamide (DMF), dimethylsulfoxide (DMSO), dimethylacetamide (DMA), n-methylpyrrolidone and mixtures thereof. The precipitating liquor is in the form of the aprotic solvent in conjunction with a certain amount of non-solvent, usually water. While this patent does not disclose a rate of production of the hollow fiber, we have found that, in accordance with the predictions of Joh et al., the Heilmann process can only be run at about 15–20 meters per minute. Further, the hollow fiber membranes produced by this process have limitations in hydrophilicity, water flux, etc. and by their very nature are limited in use to dialysis applications.

U.S. Pat. No. 4,432,875 to Wrasidlo et al., discloses reverse osmosis fiber membranes made from specific polyimide structures. Baked onto the membrane is a polymeric, high molecular weight surfactant. The polymeric surfactant apparently takes the place of the hydrophilic polymer Heilmann reference and is used to increase the wettability of the resultant fiber membrane. The fiber produced using the Wrasidlo process, however, is limited to sheet membranes that have a porosity significantly different than microporous hollow fiber membranes. Further, the "baking on" of the surfactant in Wrasidlo results in a fiber that is costly to manufacture, thus making the fiber's use economically impractical for smaller companies.

U.S. Pat. No. 3,719,640 to Le et al., discloses linear polymers of polyamide-imides having a specific formulation containing a quaternizable nitrogen atom. When nitrogen is quaternized, the polymer becomes hygroscopic and may be used as separatory membranes in such processes as desalination.

U.S. Pat. No. 4,900,449 to Kraus et al., discloses the use of polyimide polymers for pleated flat sheet type membranes. The membranes and process described are limited in use to flat sheet membranes for water filtration applications. Such membranes have less than one-half the surface area available for filtration as the filter membranes of the present invention.

Many hollow fiber membranes utilize glycerol to impart the rewetting and flux characteristics of the fiber. However, the addition of glycerol to the fiber makes the fiber costly to manufacture. Further, the glycerol must be thoroughly rinsed prior to use or it will contaminate the piping system. This makes glycerol-coated fibers inefficient, costly and time consuming for the end user. In addition, if the glycerol were not used in the fiber, the fiber would have a much lower flux rate.

While the fibers discussed above are useful in many applications, there is and always has been a trade-off among properties including tensile strength, elasticity, porosity, flux, and sieving characteristics including molecular size cutoff, solute clearance, etc. Thus, new membranes are constantly needed that can offer advantages in particular applications with given property requirements. The fiber membranes discussed above each have their own particular advantages and disadvantages, e.g., Klein teaches a fiber which can withstand high pressures present in reverse osmosis systems, Heilmann discloses a fiber which is tailored to dialysis systems, having lower flux and more stringent sieving properties, and Wrasidlo discloses membranes for reverse osmosis and filtration processes. However, not one of these references teach an asymmetric, microporous hollow fiber membrane which is biocompatible and equally suitable in processes such as hemofiltration, plasma filtration, hemodialysis and water purification and which does not use some type of polymer "additive" to render the resultant membrane hydrophilic or uses a surfactant to accomplish that goal that does not need to be "baked on."

A hollow fiber membrane that could be applied across a wide range of applications would provide a decided advantage over early hollow fiber membranes. A new and useful hollow fiber membrane is needed that incorporates a low molecular weight, surfactant which does not require the use of high temperatures to ensure the incorporation of the surfactant into and/or onto the membrane resulting in a membrane that can be autoclaved repeatedly without the loss of the rewetting characteristic and one which does not rely on glycerol for rewettability.

In addition, a new and useful membrane is needed that is chemically inert to blood and water solutions, or both, within the normal blood pH range of 7.35–7.45 and also be rewettable after repeated sterilizations. In cases where the membrane will be used for medical applications or applications involving the semi-conductor industry it would also be desirable that leachable additives such as surfactants and/or hydrophilic polymers are completely absent from the resultant fiber because residual toxic substances are a major concern. In cases where the membrane will be in contact with human blood, it is also highly desirable that the membrane be biocompatible in that it will not activate complement and that it have high sieving coefficients for middle molecules (5,000 daltons to 25,000 daltons molecular weight) such as $\beta_2$ microglobulin and myoglobin.

Further, the relatively slow rate at which related art hollow fibers are produced results in costly to manufacture microporous hollow fibers. Therefore, a new and useful process is also needed to produce the membranes of the present invention to reduce significantly the manufacture time thus ensuring that a low cost hollow fiber is available to large and small companies alike.

SUMMARY OF THE INVENTION

It is an object of the improved hollow fiber membranes provided in accordance with the present invention and the process for preparing the same to solve the problems outlined above that have heretofore inhibited the successful production of a cost-efficient membrane that has a broad range of applications.

It is also an object of the present invention to achieve a quantum jump in production rates by utilizing a sophisticated combination of process steps for the production of all hollow fiber membranes disclosed herein. A first embodiment of the present invention provides improved processing conditions that result in uniform creation of a liquid annular solution of polymer surrounding the precipitating liquid core that rapidly and uniformly solidifies into a microporous hollow fiber. Production rates can be significantly increased without failure of the hollow fiber membrane.

This unique process includes (a) passing, through an outer annular orifice of a tube-in-orifice spinneret, a polymeric solution comprising about 11 to 25 wt-% of a hydrophobic, polysulfone polymer and about 0.1 to 5 wt-% of a polyvinylpyrrolidone polymer dissolved in an aprotic solvent and having a viscosity of about 700 to 3500 cP to form an annular liquid, wherein the tube-in-orifice spinneret has an inner tube, said inner tube and said outer annular orifice each having a cross-sectional area such that the ratio of the respective cross-sectional areas of the outer annular orifice to the inner tube is about 5:1 or greater; (b) simultaneously passing, through the inner tube of the tube-in-orifice spinneret, into the center of the annular liquid, a precipitating solution comprising about 30 to 90 wt-% of a lower alcohol and about 10 to 35 wt-% of water; (c) passing the annular liquid and the precipitating solution in the center of the annular liquid through a vertical drop of at least about 1 meter in an atmosphere or an augmented atmosphere, wherein the precipitating solution interacts with the polymeric solution within the annular liquid to form an annular polymer precipitate; (d) quenching the annular polymer precipitate in a quenching bath to form a hollow fiber, wherein the spinneret and the quenching bath are separated by a vertical distance of at least about 1 meter; and (e) taking up the fiber at a rate of about 90 to about 150% of the rate at which it is formed.

A second embodiment of the present invention utilizes a microporous hollow fiber membrane incorporating a surfactant that enables the use of a unique hollow fiber that, as will be shown, has greatly improved flux and rewetting characteristics than conventional art fibers.

The hollow fiber with surfactant includes about 75 to 99 dry wt. % of a hydrophobic polysulfone polymer, about 0.1 to 20 dry wt. % of a hydrophilic polyvinylpyrrolidone polymer and an effective amount of a low molecular weight surfactant sufficient to enable the membrane to exhibit a flux of at least about $5 \times 10^{-5}$ mL/min/cm$^2$/mmHg wherein the membrane is capable of maintaining significant flux characteristics for up to at least five use and drying cycles. In addition, as will be shown, the fiber has superior rewetting characteristics, "rewetting" being defined as the ability of the fiber's flux to continuously return after at least five drying and wetting cycles.

The process for producing this unique membrane includes the steps of (a) forming an annular liquid by passing a polymeric solution comprising about 5 to 25 wt. % of a hydrophobic polysulfone polymer and about 1 to 25 wt. % of a hydrophilic polyvinyl-pyrrolidone polymer dissolved in an aprotic solvent and having a viscosity of about 100 to 10,000 cps through an outer annular orifice of a tube-in-orifice spinneret, (b) passing a precipitating solution comprising about 0.1 to 100 wt. % of an organic solvent and about 0.1 to 100 wt. % of water into the center of the annular liquid through the inner tube of the spinneret, (c) passing the polymer precipitate through the atmosphere or an augmented atmosphere, (d) quenching the polymer precipitate in a bath to form a hollow fiber, (e) contacting the polymer precipitate with a solution comprising about 0.01 to 10 wt. % of a low molecular weight surfactant, and (f) taking up the fiber at a rate of about 125–250 ft/min.

A preferred embodiment of the present invention incorporates the low molecular weight surfactant solution into the polymeric solution prior to precipitation (step (a) above) while still another embodiment contacts the surfactant solution with cut and formed bundles of hollow fibers.

One of the advantages of the hollow fiber membrane incorporating a surfactant is that hollow fibers treated with surfactant retain, as will be shown, their "rewetting" character after repeated washing and autoclaving without the use of glycerol. Another advantage of the hollow fiber membrane incorporating a surfactant is that the surfactant may be incorporated on and/or into the hollow fiber without the need to covalently bond the fiber as in heat bonded surfactant to fiber. More significantly, this provides a ready-to-use, rewettable hollow fiber membrane without the use of glycerol.

A third embodiment of the present invention provides a hollow fiber membrane incorporating a polyimide. It is an object of the hollow fiber membrane incorporating a polyimide and process for preparing the same to provide a unique hollow fiber membrane that, as will be shown, is chemically inert to aqueous solutions and/or blood, is rewettable after repeated steam and/or chemical sterilizations of at least 6–7 times, has superior clearance, sieving, and water permeability characteristics.

The hollow fiber membrane incorporating a polyimide includes about 15–25 wt. % of a fiber forming polymer selected from the group of polyimides and is characterized by the absence of polymer additives which increase wettability, wherein the hollow fiber membrane has a pore size range such that it rejects 100% of molecules (sieving coefficient of 0.0) having a molecular weight greater than about 65,000 daltons, and rejects 0.0% of molecules (sieving coefficient of 1.0) having a molecular weight of about 6,000 daltons and less, and rejects from about 35% to 0.0% of molecules (sieving coefficient of 0.65 to 1.0) having a molecular weight of 17,000 daltons; and wherein at a blood flow rate of 300 mL/min and 1.35 m$^2$ of active surface area, the fiber has clearance rates of 225–270 for urea, 200–250 for creatinine, 170–225 for phosphate, and 125–150 for Vitamin $B_{12}$ and wherein the fiber has high sieving coefficients of 0.0 for albumin, 0.65–1.0 for myoglobin, and 1.0 for inulin.

The method of manufacturing the hollow fiber membranes incorporating a polyimide includes the steps of (a) dissolving the undegraded polyimide in the appropriate solvent system (b) forming an annular liquid by passing the polymeric solution comprising about 15–25 wt. % of a highly polar polyimide dissolved in an organic solvent and having a viscosity of about 1500–5000 cps through an outer annular orifice of a tube-in-orifice spinneret, (c) passing a precipitating solution comprising about 65–99 wt. % of an organic solvent and about 35–1 wt. % of water into the center of the annular liquid through the inner tube of the spinneret, (d) passing the polymer precipitate through the atmosphere or an augmented atmosphere, (e) quenching the polymer precipitate in a bath to form a hollow fiber; and (f) taking up the fiber at a rate of about 40–70 m/min.

The most significant advantage of the hollow fiber membranes incorporating a polyimide is that membranes so formed immediately wets with aqueous solutions without the use of PVP, glycerine, or other additives. This results in an economical fiber with a homogeneous sponge structure that requires no further mechanical, chemical or other treatment to establish aqueous solution wettability.

These and other objects and advantages of the present invention will become apparent during the course of the following detailed description and appended claims. The invention may best be understood with reference to the accompanying drawings, disclosure and examples wherein an illustrative embodiment is shown.

DETAILED DESCRIPTION OF THE DRAWINGS

Figure 1:
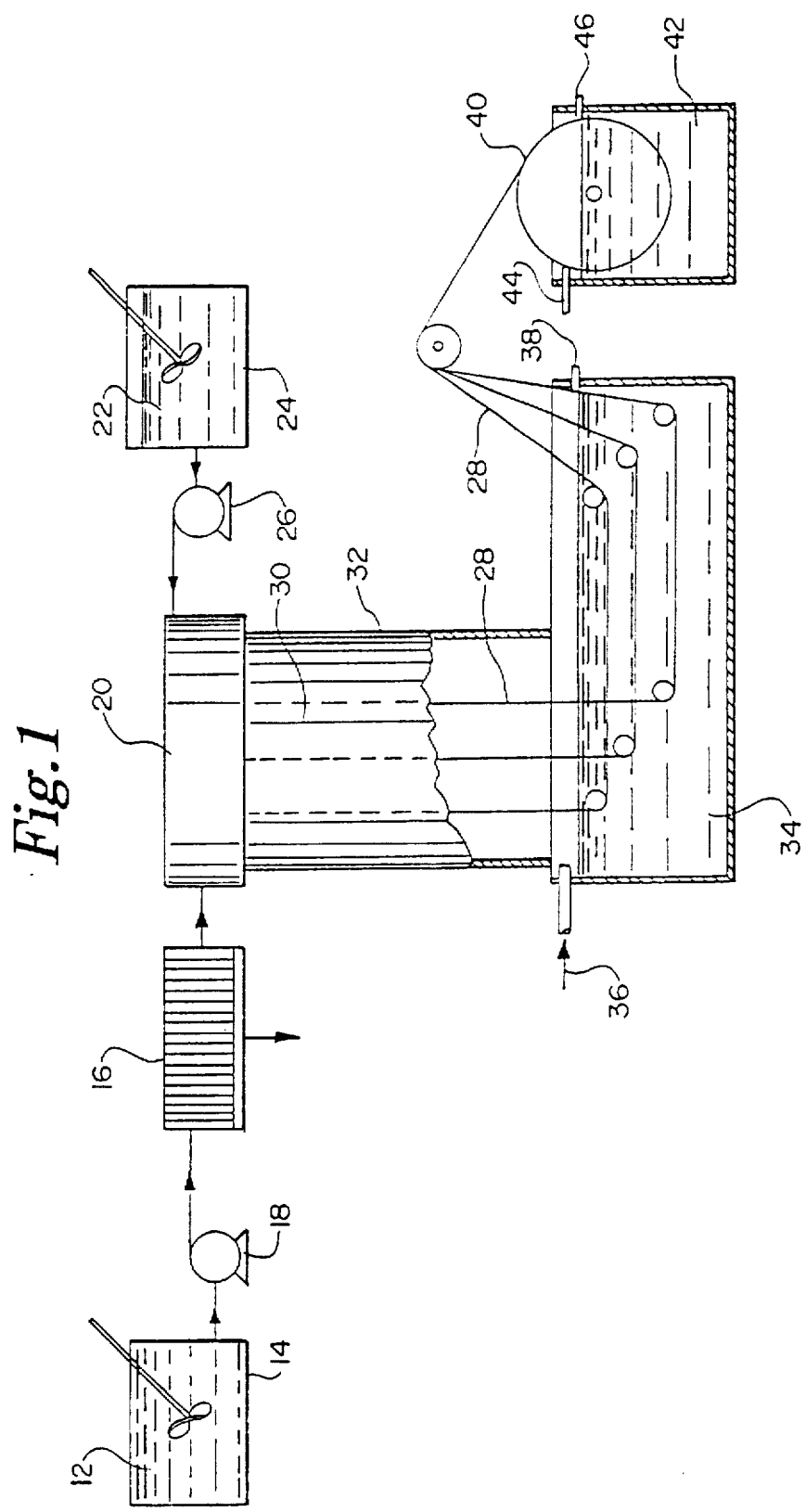
FIG. 1 is a side elevational diagram with parts cut away depicting the process of the present invention.
Figure 2:
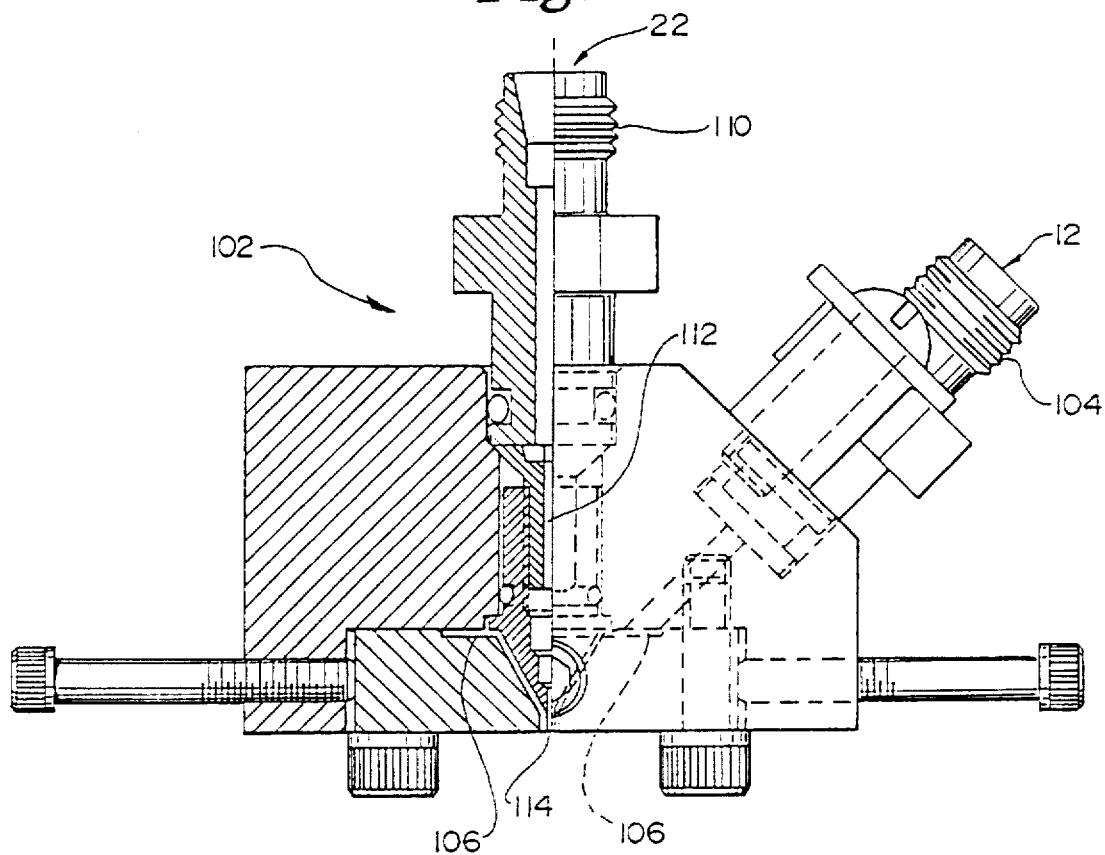
FIG. 2 is a side elevational detail view of the dry-jet wet spinning spinneret used in the process of the present invention.
Figure 3:
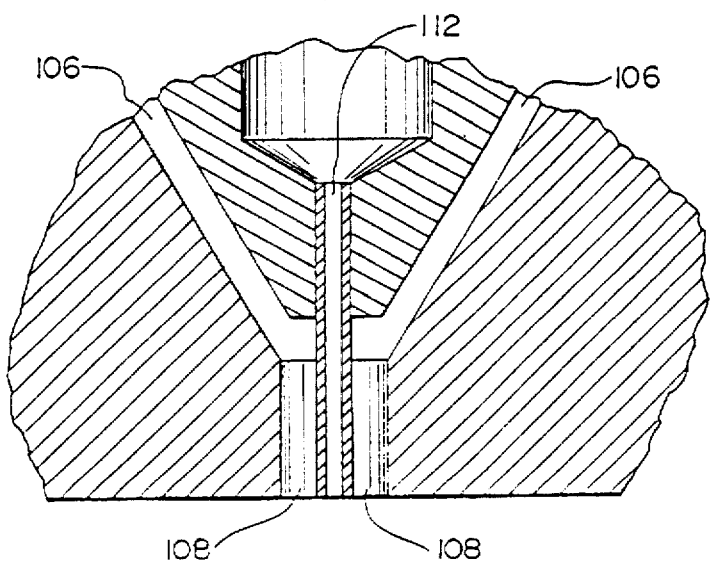
FIG. 3 is a fragmentary sectional detail view of the orifices of the spinneret.

The process of the invention may be generally determined in view of FIGS. 1-3. A polymeric dope solution 12 comprising a polysulfone polymer and a polyvinyl pyrrolidone polymer dissolved in an aprotic solvent is prepared in a mixing vessel 14. The solution is then filtered in a filter press 16 and delivered by means of a pump 18 to a dry-jet wet spinning spinneret apparatus 20. This apparatus is discussed in further detail below.

Simultaneously, a diluent or precipitating solution 22 is prepared in a second mixing vessel 24 from water and a lower alcohol. This diluent solution is also delivered to the spinneret apparatus 20 by means of pump 26. The dope solution 12 and diluent solution 22 are spun from the spinneret apparatus 20 to form a hollow fiber 28. The hollow fiber 28 drops through a volume of gaseous fluid 30 which is enclosed within a pipe 32 until the fiber reaches the surface of a quenching bath 34. Water is circulated through the quenching bath 34 in an overflow manner, i.e., a continuous flow of water 36 is supplied to the quenching bath 34, and the excess fluid overflows and is removed, e.g., at 38. The fiber 28 is then directed out of the quenching bath 34 and is wound on a take-up wheel 40 which is immersed in a second, rinsing bath 42. Again, a continuous flow of water 44 is supplied to the rinsing bath 42, and the excess fluid overflows the bath and is removed, e.g., at 46.

The hollow fiber 28 thus produced may then be removed from the take-up wheel 40 and further processed. An example of further processing includes cutting the fibers 28 to a uniform length, bundling them and drying them in any conventional manner.

A detail of a spinneret head 102 which is a part of the dry-jet wet spinning spinneret apparatus 20 is illustrated in FIGS. 2 and 3. The dope solution 12 enters through a dope port 104, is directed to an annular channel 106, and flows out of an annular orifice 108 in a generally downward direction. The diluent solution 22 enters the spinneret head 102 through a diluent port 110, is directed through an inner channel 112 and flows out through a tubular orifice 114 which is in a generally concentric orientation with respect to the annular orifice 108.

DETAILED DESCRIPTION OF THE PREFERRED EMBODIMENTS

The pore size of the membrane and the molecular weight cutoff will vary depending on the application, i.e. water filtration, ultrafiltration, hemofiltration, plasma filtration (plasmapheresis) etc. However, we define microporous generally to mean membranes having a pore size ranging substantially from about 0.001 μm to 0.5 μm. We also define "flux" or "water permeability" to mean a measure of the volume of water passed by the hollow fiber membrane under pressure for a given time and area. "Rewetting" and similar words such as rewettable, rewettability, etc., as used herein, is a description of the ability of a membrane to maintain a particular level of flux or water permeability after either cycles of wetting and drying the membrane or after steam or chemical sterilization. "Asymmetric" means that the pore size of the fiber varies from smaller to larger from the inner barrier layer to the outer sponge-like layer, respectively. "Uniformly porous" and "sponge-like" means that the porosity of the hollow fiber membrane is homogeneous throughout. In addition, "solvents with respect to the polymer" are typically aprotic solvents while "non-solvents with respect to the polymer" are typically protic solvents. "Antisolvent" is a nonsolvent with respect to the polymer and is used herein when referring to additional nonsolvents that are added to the polymeric solution. "Nonsolvents," on the other hand, are also nonsolvents with respect to the polymer, but is used herein when referring to nonsolvents added to the precipitating solution.

A. Improved Fiber Spinning Process for the Preparation of Asymmetric, Microporous, Hollow Fiber Membranes. The first embodiment of the invention is directed to a spinning process for forming microporous, hollow fibers from a polymeric solution comprising a fiber-forming polysulfone polymer, a polyvinyl pyrrolidone polymer and an aprotic solvent. The fiber forming polysulfone polymer is preferably a polyarylene sulfone. More preferably, the polysulfone polymer is a polysulfone polymer having the formula:

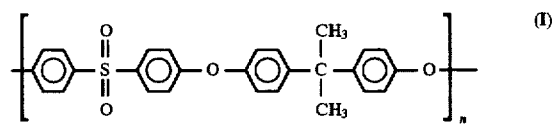

available from Amoco Chemicals Corp. under the UDEL mark, a polyether sulfone having the formula:

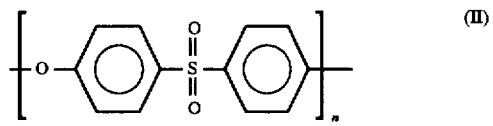

available from ICI America, Inc. under the VICTREX mark, a polyaryl sulfone, available from Amoco Chemicals Corp. under the RADEL mark, or a mixture thereof. Most preferably, the polysulfone polymer is a polysulfone of formula (I).

The polysulfone polymers preferably have a molecular weight of about 20,000 to 100,000. More preferably, the molecular weight is about 55,000 to 65,000, and most preferably, the molecular weight is about 60,000 to 65,000. If the molecular weight of the polymer is greater than about 100,000, the viscosity of the polymeric solution may become too great for processing. On the other hand, if the molecular weight of the polysulfone polymer is less than about 20,000, the viscosity of the polymeric solution may become too low to produce a fiber and any fiber formed may be too weak for processing. The polyvinyl pyrrolidone polymer (PVP) generally consists of recurring units of the formula:

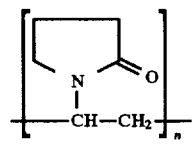

One characteristic of PVP has been called its "K-value" as defined by Fikentscher. The K-value of PVP may be calculated with the aid of the following equations:

$$\log z = c \frac{75 \ k^2}{1 + 1.5 \ kc} + k, \quad (1)$$

-continued $$K\text{-value} = \frac{\sqrt{300 c \log z + (c + 1.5 c \log z)^2} + 1.5 c \log z - c}{0.15 c + 0.003 c^2} \quad (2)$$

where z is the relative viscosity of the solution of concentration c, k is the K-value×10⁻³, and c is the concentration in % (w/v). The K-value of PVP is, therefore, a useful measure of the polymeric composition's viscosity. PVP with a K-value of about 80 to 95 is preferred in the practice of the invention. More preferably, the PVP has a K-value of about 85 to 90, and most preferably, the K-value is about 87. If the K-value of the PVP is greater than about 95, the solution may be too viscous for processing, and the pores may be too tight or small for use in hemodialysis. On the other hand, if the K-value of the PVP is less than about 80, open voids may form in the fiber wall. The PVP is useful to increase the solution viscosity of the polysulfone spinning dope. Further, this polymer is water soluble and the majority of the polymer may be dissolved from the formed fiber to increase its porosity. As some of the PVP may remain in the fiber, the fiber's wettability by an aqueous media is increased.

Finally, the polymeric solution comprises an aprotic solvent. An aprotic solvent is a solvent which is not proton-releasing under processing conditions, i.e., having non-acidic or non-ionizable hydrogen atoms. Preferably, this solvent is also soluble in water. A representative, non-limiting list of aprotic solvents useful in the invention includes dimethylformamide (DMF), dimethylsulfoxide (DMSO), dimethylacetamide (DMA), n-methylpyrrolidone and mixtures thereof. Preferably, the solvent is DMA. Depending on the desired property of the hollow fiber, a small amount of another solvent may be added instead of using a pure aprotic solvent. Preferably the additional solvent is a lower alcohol. This may enhance the precipitation of the polymer in the fiber formation.

Preferably, about 11–25 wt. %, more preferably, about 14–16 wt. %, and most preferably, about 15 wt. % of the fiber forming polysulfone polymer are dissolved in the aprotic dimethylacetamide solvent. When less than about 11 wt. % of the polysulfone polymer is used, the fibers formed are not strong enough to withstand the stresses involved in the high speed process of our invention. On the other hand, when the level of polysulfone polymer exceeds about 25 wt. %, a fiber having inferior hydraulic properties is produced.

The PVP is preferably dissolved in the solvent at a rate of about 0.1–5 wt. %, more preferably, about 2–4 wt. %, and most preferably, about 3 wt. %. When the PVP is included in the dope solution above about 5 wt. %, the resulting fibers are stiff and difficult to manufacture into dialysis cartridges. A similar result is seen when the amount of PVP is less than about 0.1 wt. %.

The polymeric solution has a viscosity of about 700–2300, preferably about 1400–1700, and most preferably, about 1500 cP at 25° C., as measured on a Brookfield viscometer. The solution is preferably filtered to remove any entrained particles (contaminants or undissolved components) to prevent apparatus blockage.

The polymeric solution is spun from the outer, annular orifice of a tube-in-orifice spinneret. A precipitating solution is delivered to the tube of the spinneret. The precipitating solution comprises a lower alcohol and water and may further comprise an aprotic solvent. To some extent, the composition of the precipitating solution affects the porosity, clearance and flux properties of the fiber. The composition of the precipitating solution effective to produce a hollow fiber membrane for use in hemodialysis is illustrated below in Table I.

TABLE I

|  | Preferred | More Preferred | Most Preferred |
|---|---|---|---|
| Lower alcohol | 30–90 wt. % | 65–90 wt. % | 75–85 wt. % |
| Water | 10–35 wt. % | 10–35 wt. % | 10–35 wt. % |

In another preferred embodiment, a precipitating solution effective to produce a hollow fiber membrane for use in a hemofilter operation may comprise the components illustrated in Table II.

TABLE II

|  | Preferred | More Preferred | Most Preferred |
|---|---|---|---|
| Lower alcohol | 30–90 wt. % | 50–80 wt. % | 60–70 wt. % |
| Water | 10–35 wt. % | 10–30 wt. % | 15–25 wt. % |
| Aprotic solvent | 0–50 wt. % | 5–35 wt. % | 10–20 wt. % |

In yet another preferred embodiment, a precipitating solution effective to produce a hollow fiber membrane for use in a blood filter to separate red blood cells from higher molecular weight materials may comprise the components illustrated in Table III.

TABLE III

|  | Preferred | More Preferred | Most Preferred |
|---|---|---|---|
| Lower alcohol | 30–90 wt. % | 30–60 wt. % | 35–45 wt. % |
|  | 10–35 wt. % | 10–30 wt. % | 15–25 wt. % |
| Aprotic solvent | 0–50 wt. % | 20–50 wt. % | 35–45 wt. % |

Representative, non-limiting examples of lower alcohols include methanol, ethanol, n-propanol, iso-propanol, n-butanol, t-butyl alcohol, isobutyl alcohol or a mixture thereof. Preferably, the alcohol comprises methanol, ethanol, n-propanol, isopropanol, n-butanol or a mixture thereof. More preferably, the alcohol comprises isopropanol.

The water which may be used in the precipitating liquid may be tap water, deionized water or water which is a product of reverse osmosis. Preferably the water is deionized water which has first been treated by reverse osmosis.

The aprotic solvent used in the precipitating solution may again be dimethylformamide (DMF), dimethylsulfoxide (DMSO), dimethylacetamide (DMA), n-methylpyrrolidone and mixtures thereof. Preferably, the aprotic solvent is the same as that used in the polymeric fiber forming solution. More preferably, the aprotic solvent comprises DMA.

The proportions of the alcohol, water and aprotic solvent which make up the precipitating solution influence the morphology, clearance, permeability, selectivity etc. of the hollow fiber membrane. In particular, the absence of an aprotic solvent in the precipitating solution may result in lower poor size and lower flux in the resulting fiber. It is generally preferred that the proportion of water in the precipitating solution remain relatively low, about 10 to 35 wt. %, to ensure proper fiber results less than about 10 wt. % of water may result in too slow of a precipitation of the polymers to form a fiber, and a concentration of water greater than about 35 wt. % may result in a decrease in flux and pore size.

As indicated above, the polymeric dope is pumped and filtered and directed to the outer, ring orifice of a tube in orifice spinneret. At the same time, the precipitating liquid is pumped to the inner coaxial tube of the spinneret. These two solutions are then delivered from the spinneret in a manner such that the polymer dope forms an annular sheath surrounding a flow of precipitating liquid within the annulus. Preferably, the spinneret head is maintained at a temperature of about 5°–85° C., more preferably, about 15°–25° C., and most preferably, about 18° C. The polymeric dope is subjected to a pressure of about 01400 kPa, more preferably, about 140–1000 kPa, and most preferably, about 350–850 kPa. In a preferred embodiment, the polymer dope is spun through a ring orifice having an outside diameter of about 0.018 inches (about 460 microns) and an inside diameter of about 0.008 inches (about 200 microns).

At the same time, precipitating liquid is pumped through the tube of the spinneret at a pressure of about 01000 kPa, preferably about 0–100 kPa, and most preferably, about 1–20 kPa. In a preferred embodiment, the precipitating liquid or diluent solution is delivered through a tube having an inside diameter of about 0.004 inches (about 100 microns).

In a preferred embodiment, in order to produce a hollow fiber having a 280 micron outside diameter and 200 micron inside diameter, the polymer dope is delivered to the spinneret at a rate of at least about 0.1 mL/min, more preferably, about 2–10 mL₁/min, most preferably, about 3 mL/min, and the precipitating liquid is delivered at a rate of at least about 0.1 mL/min, more preferably, about 2–10 mL/min, and most preferably, about 3 mL/min. The spinneret is oriented in a manner such that fiber production is driven by fluid flow and by removal from the spinneret by gravity effects. Preferably, the fiber emerges from the spinneret and is pulled by gravity in a nearly vertical direction downwards.

In order to provide satisfactory fibers in the practice of the invention, laminar fluid flow should be maintained both within the spinneret head and the spun fluids which interact to precipitate the fiber. If turbulent flow is present in the spinneret head, especially within the channels which convey the polymeric dope, gas pockets may develop and ultimately form large voids in the spun fiber. Turbulent flow within the spun fluids may also result in voids within the fiber. It may be helpful to describe the relative flow rates of the polymeric dope to the diluent solution. Preferably, the volumetric flow ratio of dope to diluent is from about 0.1:1 to about 10:1, more preferably, the ratio is about 0.25:1 to 4:1, and most preferably, the ratio of the polymeric dope to diluent flow rate is about 0.7:1 to 1.5:1.

It is helpful to visualize the spinneret dimensions by resort to ratios of the annular orifice for passage of the polymeric dope and the coaxial tubular orifice for passage of the diluent or precipitating solution. One helpful ratio is the ratio of the cross-sectional area of the annular orifice to tubular orifice. Preferably, the ratio is greater than about 5:1, more preferably, the ratio is about 10:1 to 25:1, and most preferably, the ratio of the annular orifice to tubular orifice cross-sectional area is about 16:1. Another helpful dimensional ratio is the annular ring thickness to tube inside diameter. Preferably, the ratio is greater than about 0.5:1, more preferably, the ratio is about 0.75:1 to 5:1, and most preferably, the ratio of the annular ring thickness to tube inside diameter is about 1:1 to 2:1. A third helpful dimensional ratio is the outside diameter of the annular orifice to tube inside diameter. Preferably, this ratio is greater than about 2:1, more preferably, the ratio is about 3:1 to 15:1, and most preferably, the ratio of the annular outside diameter to tube inside diameter is about 4:1 to 5:1.

As the fiber emerges from the spinneret, it travels in a substantially downward vertical direction over a distance of about 0.1–10 m, more preferably, about 1–3 m, and most preferably, about 1.5 m. This allows the precipitating liquid to substantially precipitate the polymer in the annular dope solution forming the solid fiber capillary before it is immersed in a quenching solution. Between the spinneret and the quenching bath, the fiber can travel through the atmosphere, air, an augmented atmosphere i.e., a mixture of air and a gas, an inert gas, or a mixture thereof. Preferably, for ease in processing, and to produce a high quality fiber, the fiber travels through air with a relative humidity of about 40–50%. This gaseous atmosphere may be relatively stagnant, or there can be fluid flow. Preferably, the flow rate is sufficient to allow complete air change over in the spinning environment once every 30 minutes. In one preferred embodiment the gas flow is about 10 L/min.

Next, the fiber is submerged in a tank comprising water and 0–10 wt. % other materials. Again, the water may be tap, deionized water, or the product of a reverse osmosis process. The temperature of the quenching bath is preferably between about 0° C.–100° C., more preferably, about 15° C.–45° C., and most preferably, about 35° C. The water temperature can affect the performance of the fiber. Lower temperatures can reduce the flux of the resulting fiber. Increasing the quenching bath temperature can increase the flux of the fiber. However, the temperature of the quenching bath does not seem to affect solute clearance rates greatly.

The fiber is preferably immersed in this quenching bath for a period of about 0.1–10 minutes, preferably about 0.15 minutes, and most preferably, about 1 minute. This residence time substantially permits the full precipitation of the polysulfone polymer to form the microporous hollow fiber. This quenching bath also helps to remove the excess, unprecipitated polymers as well as some of the PVP, the water soluble solvent and precipitating liquid.

After the quenching bath, the fiber may further be rinsed to remove further unprecipitated polymers and solvents. This rinsing may be accomplished in a one stage or multiple stage bath arrangement. Preferably, the rinsing is achieved in a two stage bath having a water temperature of about 0° C.–100° F. in the first stage, more preferably, about 15° C.–45° C., and most preferably, about 35° C. and a temperature of about 0° C.–100° C., more preferably, about 15° C.–45° C., and most preferably, about 35° C. in a second stage. The fiber is then wound up on a take up reel. This take up reel is preferably rotating at a speed such that the fiber is being wound at about 90–150% of the rate at which it is being formed at the spinneret. More preferably, the fiber is being wound at a rate substantially equal to that at which it is being produced, i.e., there is no draft.

The hollow fibers may then be dried, texturized, cut to a desired length, or further processed to form useful articles including hemodialyzer, hemofilters, blood filters, water filters, etc, having performance levels at least equivalent to currently available hollow fiber membranes.

For example, at a 200 mL/min flow rate, a clearance rate of at least about 130 mL/min is possible for both urea and creatinine and at least about 80 mL/min for vitamin $B_{12}$. The flux rate possible with the fibers of the present invention is up to about 50 mL/min/cm²/mmHg, preferably about 10 to 25 mL/min/cm²/mmHg. The percent rejection for BSA is preferably less than about 5%, more preferably, about 2–3%.

EXAMPLES

The following specific examples which contain the best mode, can be used to further illustrate the invention. These examples are merely illustrative of the invention and do not limit its scope.

Example 1

A polymeric dope solution was formed by dissolving 16.2 wt. % of a polysulfone polymer having a molecular weight of about 55,000 to 60,000 (UDEL P1800 available from Amoco) and 4.8 wt. % polyvinyl pyrrolidone polymer (PVP) having a K-value of about 85–88 in dimethylacetamide (DMA). The material was filtered and then pumped to a tube-in-orifice spinneret at a rate of 3.1 mL/min and a temperature of about 35° C.

Simultaneously, a diluent solution consisting of 70.5 wt. % isopropanol and 29.5 wt. % reverse osmosis, deionized (r.o.,d.i.) water was mixed, filtered and delivered to the spinneret at a temperature of about 20° C. and a rate of about 3 mL/min.

The polymeric dope solution was delivered through the outer, annular orifice of the spinneret having an outside dimension of about 0.018 inches (about 460 microns) and an inside dimension of about 0.008 inches (about 200 microns). The diluent was delivered through a tube orifice within the annular orifice having an inside diameter of about 0.004 inches (about 100 microns). The spinneret head was maintained at about 19° C. by means of a water bath. The spinneret discharged the column of dope solution and diluent downward through a six-inch diameter LEXAN pipe enclosing a volume of nitrogen (circulating at about 10 L/min) for a distance of about 1.5 m into a quenching water bath. The quenching bath was maintained at about 45° C., and about 5.5 L/min of reverse osmosis (r.o.) water was pumped into the tank with resulting water overflow. The fibers were then wound on a take-up wheel immersed in a second reverse osmosis water bath maintained at about 45° C., and about 6.8 L/min of r.o. water was pumped into the bath with resulting water overflow. The take-up rate was about 85 m/min. Simultaneously, the wheel was subjected to a water spray at about 65° C.

The fiber was then removed from the take-up wheel, cut and formed into bundles of about 9025 fibers about 25 cm long. These bundles were then immersed in a soaking water bath maintained at about 55° C. for about 10 hours. Water (r.o.) was circulated in an overflow manner at a rate of about 1 L/min. Afterward, the fiber bundles were dried and tested.

Example 2

The above procedure was repeated using the dope and diluent solutions of Example 1. The spinneret conditions of Example 1 were also repeated, but the fibers were spun into the ambient atmosphere (not a nitrogen atmosphere).

The quenching bath was maintained at about 110° F. and was fed with about 2.3 L/min r.o. water. The second bath was maintained at about 40° C. and was fed with about 5.5 L/min r.o. water. The water spray was maintained at about 35° C., and the take-up rate was about 90 m/min.

The resulting fiber bundles were soaked for about 1 hour at about 55° C. at a water flow rate of about 1 L/min and were thereafter dried.

Example 3

The above procedure was repeated using a dope solution comprising about 13.1 wt. % of the polysulfone of Example 1 and about 2.8 wt. % of PVP having a K-value of about 85–88 in DMA and a diluent solution comprising about 87 wt. % isopropyl alcohol and about 13 wt. % r.o.,d.i. water. The resulting dope solution had a viscosity of about 750 cP at 25° C. The dope solution was supplied to the spinneret at room temperature and a rate of about 0.89 mL/min, and the diluent solution was supplied at a rate of about 0.85 mL/min at room temperature. The spinneret head was maintained at about 21° C. The fiber was spun into the ambient atmosphere. The quenching bath was maintained at about 90° F. and was fed with about 7.6 L/min r.o. water. The second bath was maintained at about 90° F. and was fed with about 2 L/min r.o. water. The water spray was maintained at about 25° C., and the take-up rate was about 30 m/min.

The resulting fiber bundles were soaked for about 6 hours at about 55° C. at a water flow rate of about 1 L/min and were thereafter dried and tested. The fiber bundles exhibited good solute clearance and flux.

Example 4

The procedure of Example 1 was repeated using a dope solution comprising about 15.1 wt. % of the polysulfone of Example 1 and about 2.8 wt. % of PVP having a K-value of about 85–88 in DMA and a diluent solution comprising about 70.5 wt. % isopropyl alcohol and about 29.5 wt. % r.o.,d.i. water. The resulting dope solution had a viscosity of about 1220 cP at 25° C. The dope solution was supplied to the spinneret at about 23° C. and a rate of about 3.1 mL/min, and the diluent solution was supplied at a rate of about 3 mL/min at room temperature. The spinneret head was maintained at about 24° C. The fiber was spun into the ambient atmosphere.

The quenching bath was maintained at about 90° F. and was fed with about 7.6 L/min r.o. water. The second bath was maintained at about 30° C. and was fed with about 2 L/min r.o. water. The water spray was maintained at about 20° C., and the take-up rate was about 75 m/min.

The resulting fiber bundles were soaked for about 5 hours at about 55° C. at a water flow rate of about 1 L/min and were thereafter dried and tested. The fiber bundles exhibited good solute clearance, flux and strength.

Example 5

The procedure of Example 1 was repeated using a dope solution comprising about 14.1 wt-% of the polysulfone of Example 1 and about 2.8 wt. % of PVP having a K-value of about 85–88 in DMA and a diluent solution comprising about 87 wt. % isopropyl alcohol and about 13 wt. % r.o.,d.i. water. The resulting dope solution had a viscosity of about 890 cP at 25° C. The dope solution was supplied to the spinneret at about 20° C. and a rate of about 0.89 mL/min, and the diluent solution was supplied at a rate of about 0.85 mL/min at about 20° C. The spinneret head was maintained about 23° C. The fiber was spun into the ambient atmosphere.

The quenching bath was maintained at about 32° C. and was fed with about 8 L/min r.o. water. The second bath was maintained at about 32° C. and was fed with about 2 L/min r.o. water. The water spray was maintained at about 25° C., and the take-up rate was about 300 m/min.

The resulting fiber bundles were soaked at about 35° C. at a water flow rate of about 2 L/min and were thereafter dried and tested. The fiber bundles exhibited good solute clearance and flux.

Example 6

The procedure of Example 1 was repeated using a dope solution comprising about 15.1 wt. % of a polysulfone polymer having a molecular weight of about 60,000 to 65,000 (UDEL P1835 from Amoco) and about 2.8 wt. % of PVP having a K-value of about 85–88 in DMA and a diluent solution comprising about 80 wt. % isopropyl alcohol and about 20 wt. % r.o.,d.i. water. The resulting dope solution had a viscosity of about 1520 cP at 25° C. The dope solution was supplied to the spinneret at about 37° C. and a rate of about 3.55 mL/min. and the diluent solution was supplied at a rate of about 2.5 mL/min. The spinneret head was maintained at about 26° C. The fiber was spun into the ambient atmosphere.

The quenching bath was maintained at about 35° C. and was fed with about 4 L/min r.o. water. The second bath was maintained at about 35° C. and was fed with about 2 L/min r.o. water. The water spray was maintained at about 25° C., and the take-up rate was about 80 m/min.

The resulting fiber bundles were soaked for about 8 hours at about 55° C. at a water flow rate of about 1 L/min and were thereafter dried and tested. The fiber bundles exhibited good solute clearance, flux and strength.

Example 7

The procedure of Example 1 was repeated using a dope solution comprising about 16.1 wt. % of the polysulfone of Example 1 and about 4.8 wt. % of PVP having a K-value of about 85–88 in DMA and a diluent solution comprising about 70.5 wt. % isopropyl alcohol and about 29.5 wt. % r.o.,d.i. water. The resulting dope solution had a viscosity of about 3500 cP at 25° C. The dope solution was supplied to the spinneret at about 37° C. and a rate of about 1.3 mL/min, and the diluent solution was supplied at a rate of about 1.3 mL/min at about 20° C. The spinneret head was maintained at about 23° C. The fiber was spun into the ambient atmosphere.

The quenching bath was maintained at about 30° C. and was fed with about 6 L/min r.o. water. The second bath was maintained at about 30° C. and was fed with about 4 L/min r.o. water. The water spray was maintained at about 20° C., and the take-up rate was about 40 m/min.

The resulting fiber bundles were soaked for about 6 hours at about 55° C. at a water flow rate of about 2 L/min and were thereafter dried and tested. The fiber bundles exhibited good solute clearance, flux and strength.

Example 8

The procedure of Example 1 is repeated using a dope solution comprising about 15.1 wt. % of UDEL 1835 and 2.8 wt. % PVP having a K-value of about 85–88 in DMA and a diluent solution comprising about 79 wt. % isopropyl alcohol and about 21 wt. % r.o.,d.i. water. The dope solution is supplied to the spinneret at about 37° C. and a rate of about 3.55 mL/min, and the diluent solution is supplied at a rate of about 2.5 mL/min at about 20° C. The fiber is spun into the ambient atmosphere.

The quenching bath is maintained at about 35° C. and is fed with about 4 L/min r.o. water. The second bath is maintained at about 35° C. and is fed with about 9 L/min r.o. water. There is no water spray present.

The resulting fiber bundles are soaked in water at about 55° C. and are thereafter dried and tested. The fiber bundles exhibit good solute clearance, flux and strength.

Example 9

The procedure of Example 1 was repeated using a dope solution comprising about 16.1 wt. % of the polysulfone of Example 1 and about 2.8 wt. % of PVP having a K-value of about 85–88 in DMA and a diluent solution comprising about 70.5 wt. % isopropyl alcohol and about 29.5 wt. % water. The resulting dope solution had a viscosity of about 1540 cP at 25° C. The dope solution was supplied to the spinneret at about 20° C. and a rate of about 3.1 mL/min, and the diluent solution was supplied at a rate of about 3 mL/min at about 20° C. The spinneret head was maintained at about 25° C. The fiber was spun into the ambient atmosphere.

The quenching bath was maintained at about 30° C. and was fed with about 4 L/min r.o. water. The second bath was maintained at about 30° C. and was fed with about 6 L/min r.o. water. The water spray was maintained at about 25° C., and the take-up rate was about 85 m/min.

The resulting fiber bundles were soaked for about 5 hours at about 55° C. at a water flow rate of about 2 L/min and were thereafter dried and tested. The fiber bundles exhibited good solute clearance, flux and strength.

Example 10

The procedure of Example 1 was repeated using a dope solution comprising about 16.1 wt. % of the polysulfone of Example 1, about 4.8 wt. % of PVP having a K-value of about 85–88, about 2 wt. % of ethanol and the balance of DNA and a diluent solution comprising about 70.5 wt. % isopropyl alcohol and about 29.5 wt. % water. The resulting dope solution had a viscosity of about 2770 cP at 25° C. The dope solution was supplied to the spinneret at about 37° C. and a rate of about 3.1 mL/min, and the diluent solution was supplied at a rate of about 3 mL/min at room temperature. The spinneret head was maintained at about 24° C. The fiber was spun into the ambient atmosphere.

The quenching bath was maintained at about 37° C. and was fed with about 4 L/min r.o. water. The second bath was maintained at about 37° C. and was fed with about 2 L/min r.o. water. The water spray was maintained at about 45° C., and the take-up rate was about 80 m/min.

Example 11

The procedure of Example 1 was repeated using a dope solution comprising about 15.1 wt. % of a polysulfone polymer having a molecular weight of about 60,000 to 65,000 (UDEL P1835 from Amoco) and about 2.8 wt. % of PVP having a K-value of about 85–88 in DMA and a diluent solution comprising about 81 wt. % isopropyl alcohol and about 19 wt. % r.o.,d.i. water. The dope solution was supplied to the spinneret at about 34° C. and a rate of 3.55 mL/min, and the diluent solution was supplied at a rate of about 2.5 mL/min. The spinneret head was maintained at about 19° C. The fiber was spun into the ambient atmosphere.

The quenching bath was maintained at about 17° C. and was fed with about 6 L/min r.o. water. The second bath was maintained at about 35° C. and was fed with about 2 L/min r.o. water. There was no water spray, and the take-up rate was about 80 m/min.

The resulting fiber bundles were soaked in water at, about 55° C., and were thereafter dried and tested. The fiber bundles exhibited good solute clearance, moderate flux and good strength.

Example 12

The procedure of Example 1 was repeated using a dope solution comprising about 15.1 wt. % of a polysulfone polymer having a molecular weight of about 60,000 to 65,000 (UDEL P1835 from Amoco) and about 2.8 wt. % of PVP having a K-value of about 85–88 in DMA and a diluent solution comprising about 82 wt. % isopropyl alcohol and about 18 wt. % r.o.,d.i. water. The dope solution was supplied to the spinneret at about 34° C. and a rate of about 3.55 mL/min, and the diluent solution was supplied at a rate of about 2.5 mL/min. The spinneret head was maintained at about 20° C. The fiber was spun into the ambient atmosphere.

The quenching bath was maintained at about 16° C. and was fed with about 6 L/min r.o. water. The second bath was maintained at about 36° C. and was fed with about 2 L/min r.o. water. There was no water spray, and the take-up rate was about 80 m/min.

The resulting fiber bundles were soaked in water at about 55° C. and were thereafter dried and tested. The fiber bundles exhibited good solute clearance, moderate flux and good strength.

Fibers from Examples 6, 11 and 12 were evaluated for water flux and compared. The results are shown below in Table IV.

TABLE IV

| Example | Flux* |
|---------|-------|
| 6       | 18–26 |
| 11      | 11    |
| 12      | 9     |

*(mL × 10⁻⁵/min/cm²/mmHg)

Example 13

Following the general procedure of Example 1, a polymeric dope comprising 17.2 wt. % of the polysulfone of Example 1, 2.8 wt. % PVP K90 and 80 wt. % dimethylacetamide was spun with an isopropyl alcohol/water diluent solution. Fibers were spun under the conditions indicated in Table V. From the data of Table V, it can be seen that increasing moisture in the spinning atmosphere decreases the flux of the resulting fiber and decreases the pore size of the fiber.

TABLE V

EFFECT OF ENCLOSURE AND ENCLOSURE CONDITIONS AROUND FIBER DROP AREA ON FIBER PERFORMANCE

|  | Flux* | % Rejection BSA |
|---|---|---|
| No Enclosure | 87.9 | 1.0 |
| Enclosure | 69.2 (dry N2 at 10 Lpm) | 3.7 |
| Enclosure | 57.9 (No Air Flow) | 1.0 |
| Enclosure | 44.6 (Water Sat. Air at 10 Lpm) | 7.7 |

*Solution of BSA in water (mL × 10⁻⁵/min/cm²/mmHg)

Example 14

The basic procedure of Example 1 was repeated using a polymeric solution comprising 7.1 wt. % of the polysulfone of Example 1, 2.8 wt. % PVP K90, 75.8 wt. % dimethylacetamide, 8.4 wt. % dimethylformamide, and 1.9 wt. % water. This dope was spun with diluent formulations as indicated in Table VI. From the data in Table VI, it can be seen that the use of an aprotic solvent increases the flux of the resulting fiber and that using a major proportion of water also increases the flux of the resulting fiber.

TABLE VI

EFFECT OF DIFFERENT ORGANICS IN THE DILUENT ON POLYSULFONE/PVP FIBER PERFORMANCE

| Diluent Formulation | | | | % Rejection | |
|---|---|---|---|---|---|
| Material | % | Material | % | Flux* | BSA | Myoglobin |
| Water | 75 | Methanol | 25 | 3.8 | 100 | 88 |
| Water | 50 | Methanol | 50 | 1.8 | 100 | 96 |
| Water | 25 | Methanol | 75 | Unit Not Tested | | |
| Water | 75 | N-Methyl Pyrrolidone | 25 | 5.5 | 98 | 69 |
| Water | 50 | N-Methyl Pyrrolidone | 50 | 100 | 96 | |
| Water | 25 | N-Methyl Pyrrolidone | 75 | Could Not Spin Fiber | | |

*(mL × 10⁻⁵/min/cm²/mmHg)

Example 15

The general procedure of Example 1 was repeated using a polymer dope comprising about 11.1 wt. % of the polysulfone of Example 1, about 2.8 wt. % PVP K90, about 77.5 wt. % dimethylacetamide, and about 8.6 wt-% dimethylformamide and an isopropyl alcohol/water diluent solution. These compositions were spun having the drop heights shown in Table VII. The data in Table VII indicates that there is little change in fiber performance with the variation in fiber drop height.

TABLE VII

EFFECT OF WATER LEVEL IN THE POLYSULFONE/PVP/DMAC FORMULATION AND EFFECT OF DROP HEIGHT (FREE FALL FIBER DROP) ON FIBER SIZE AND PERFORMANCE

| | | | % Rejection | |
|---|---|---|---|---|
| Drop Height | I.D.* | Flux* | BSA | Myoglobin |
| 35" | 212 | 52.8 | 57.2 | 18.8 |
| 45" | 216 | 49.5 | 60.5 | 8.1 |

*Inside diameter of resulting fiber (microns)
**(mL × 10⁻⁵/min/cm²/mmHg)

Example 16

The general procedure of Example 1 was again repeated with a polymeric dope consisting of about 13.6 wt. % of the polysulfone of Example 1, about 3.4 wt. % PVP K90, about 1.0 wt. % water and about 82 wt. % dimethylacetamide. Diluent solutions have the formulations shown in Table VIII were spun with this dope composition. The data in Table VIII indicates that in diluent solutions comprising a major proportion of alcohol, decreasing water concentrations increase the flux of the resulting fibers.

TABLE VIII

RELATIONSHIP OF ISOPROPANOL IN THE DILUENT (WATER/ISOPROPYL MIX) ON POLYSULFONE/PVP FIBER PERFORMANCE

| | Flux* | % Rejection BSA |
|---|---|---|
| 85% IPA | 121 | 70 |
| 70% IPA | 23 | 95.7 |
| 60% IPA | 10 | 98.2 |

*Solution of BSA in water (ml × 10⁻⁵/min/cm²/mmHg)

B. Asymmetric, Microporous, Hollow Fiber Membrane Incorporating a Surfactant. The second embodiment of the present invention is directed to a microporous, hollow fiber that includes a hydrophobic polymer, a hydrophilic polymer and a low molecular weight surfactant. When used as a water filter, the pore size of the microporous, hollow fiber membrane incorporating a surfactant is typically from about 0.005 μm to 0.5 μm with the average pore size being from about 0.05 μm to about 0.1 μm.

The hydrophobic polymer is preferably a polysulfone polymer, polyethersulfone, poly(arylsulfone), poly(aryl ether sulfone) or a poly(phenylsulfone). The polysulfone polymer is preferably a poly(arylsulfone). More preferably, the polysulfone polymer is a poly(oxy-1,4-phenylene sulfonyl-1,4-phenyleneoxy-1,4phenyleneisopropylidene-1, 4phenylene) polymer having the formula (—OC$_6$H$_4$C(CH$_3$)$_2$C$_6$H$_4$SO$_2$C$_6$H$_4$—)$_n$ with the accompanying structure:

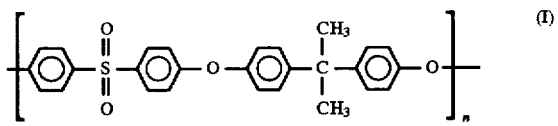

available from Amoco Chemicals Corp. (Atlanta, Ga.)) under the UDEL mark; or a polyether sulfone having the formula (—O—C$_6$H$_4$SO$_2$C$_6$H$_4$—) with the accompanying structure:

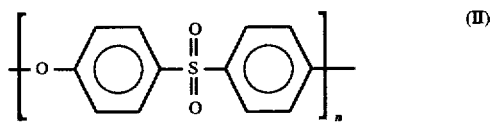

available from ICI Americas, Inc. (Wilmington, Del.) under the VICTREX mark; or a poly(arylsulfone) available from Amoco Chemicals Corp. (Atlanta, Ga.) under the RADEL mark, or a mixture thereof. Most preferably, the polysulfone polymer is a polysulfone of formula (I).

The polysulfone polymers preferably have a molecular weight of about 20,000 to 100,000. More preferably, the molecular weight is about 55,000 to 65,000 and most preferably, the molecular weight is about 60,000 to 65,000. If the molecular weight of the polymer is greater than about 100,000, the viscosity of the polymeric solution may become too great for processing. On the other hand, if the molecular weight of the polysulfone polymer is less than about 20,000, the viscosity of the polymeric solution may become too low to produce a fiber and any fiber formed may be too weak for processing.

The hydrophilic polymer not only supplies hydrophilicity to the hollow fiber membrane but also markedly improves its porosity as well. The hydrophilic polymer may be water soluble cellulose, starch derivatives, polyvinylpyrrolidone, polyethylene glycols. Preferably, the hydrophilic polymer is polyvinylpyrrolidone ("PVP").

The PVP generally consists of recurring units of the formula (—C(C$_4$H$_6$NO)HCH$_2$—)$_n$ with the accompanying structure:

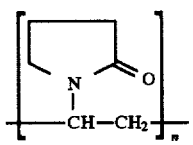

The PVP is useful to increase the solution viscosity of a polymeric spinning solution or dope. Further, this polymer is water soluble and the majority of the polymer may be dissolved from the formed fiber to increase its porosity. As some of the PVP may remain in the fiber, the fiber's wettability by an aqueous media is increased.

However, to further increase the wettability of the fiber by an aqueous media, the fiber incorporates a low molecular weight surfactant. This surfactant may be amphoteric, zwitterionic, nonionic, anionic, cationic, or the surfactant may include a mixture of surfactant types. A representative, non-limiting list of useful amphoteric surfactants includes lauroamphocarboxyglycinate, e.g., MIRANOL 2MHT MOD available from Miranol, Inc. (Dayton, N.J.) or synergistic constituents thereof. A representative, non-limiting list of useful zwitterionic surfactants includes B-N-alkylaminopropionic acids, N-alkyl-B-iminodipropionic acids, fatty acid imidazoline carboxylales, N-alkyl betaines, sulfobetaines, sultaines, and amino acids (e.g., asparagine, L-glutamine, etc.). A representative, nonlimiting list of useful nonionic surfactants include alkoxylated alkylamines, ethanol, isopropanol, methanol glycerine, alkylpyrrolidones, linear alcohol alkoxylates, difunctional block copolymer surfactants with terminal secondary hydroxyl groups, difunctional block copolymers with terminating primary hydroxyl groups, fluorinated alkyl esters, N-alkylpyrrolidones, alkoxylated amines, and poly (methylvinylether/maleic anhydride) derivatives. Other suitable surfactants would include oligomeric or non-monomeric species containing a C12-18 aliphatic and/or aromatic hydrophobic moiety and a hydrophilic functionality within the same molecule. A representative, non-limiting list of anionic surfactants include aromatic hydrophobic based acid esters and anionic flourochemical surfactants. A representative, non-limiting list of cationic surfactants includes methylbis-hydrogenated tallow amido-ethyl, 2-hydroxy-ethyl ammonium methyl sulfate, water soluble quaternized condensate polymers, and cocoalkyl bis (2-hydroxyethyl) methyl, ethoxylated chlorides. Preferably, the surfactant is an aromatic hydrophobic based acid ester, an alkoyxlated fatty amine, an alkoxylated alkylamine or a lauroampho-diacetate/sodium trideceth sulfate. More preferably, the surfactant is an alkoxylated cocoamine. Most preferably, the surfactant is an ethoxylated (2–15 EO) cocoamine.

The preferred embodiment utilizes a low molecular weight surfactant. Thus, useful surfactants are generally non-polymeric and/or oligomeric surfactants having molecular weights of less than about 2,000. Preferably, the surfactant has a molecular weight of about 300 to 1,500, more preferably, about 700 to 1,200, and most preferably about 800 to 1,000. If the molecular weight of the water soluble surfactant is too high, longer soaking and rinsing times would be required in most cases, interfering with the efficiency of the process. On the other hand, if the molecular weight of the water soluble surfactant is too low the surfactant may wash off too quickly resulting in an unwettable fiber. Naturally however, this is contingent upon the particular surfactant's critical micelle concentration (CMC) which allows one to draw comparisons between theoretical monolayer coverage (i.e surfactant to surface area) and performance and solvating characteristics such as dependence on pH, dissolved solids which affect the efficiency of a given surfactant toward fiber coverage.

For reasons of cost and effectiveness, it is preferred that the final fiber prior to potting contains from substantially about 0.001% to 10.0% by weight of the surfactant (1.0× $10^{-5}$ g to 0.1 g of surfactant/1 g of fiber), more preferably from substantially about 0.1% to 2.0% by weight of the surfactant (0.001 g to 0.02 g of surfactant/1 g of fiber) and most preferably from substantially about 0.1% to 0.5% by weight of the surfactant (0.01 g to 0.05 g of surfactant/1 g of fiber) when the surfactant is incorporated into the polymeric dope solution in accordance with the present invention.

When the surfactant is contacted with the formed fiber in the quenching bath series or when bundles of fibers are soaked in the surfactant solution, it is preferred that the final fiber prior to potting contains from substantially about 0.001% to 10.0% by weight of the surfactant ($1.0 \times 10^{-5}$ g to 0.1 g of surfactant/1 g of fiber), more preferably from substantially about 0.1% to 2.0% by weight of the surfactant (0.001 g to 0.02 g of surfactant/1 g of fiber) and most preferably from substantially about 0.1% to 0.5% by weight of the surfactant (0.00 g to 0.05 g of surfactant/1 g of fiber). It is also preferred that the final fiber after potting contains amounts of surfactant substantially equal to those designated above.

It should be noted that the actual concentration of surfactant in the soaking solution is dictated by processing restraints. At higher concentrations, flush time needed to remove excess surfactant from the fiber is increased. At lower concentrations, longer soaking times are required to obtain effective membranes.

The surfactant interacts with the hollow fiber to become associated with the fiber probably through an absorption and/or adsorption phenomenon, i.e., the surfactant is co-miscible with and/or absorbed on the fiber surface. The inventors hypothesize that this is most likely accomplished by hydrogen bonding, dipole-dipole attractions and Van der Walls forces. There is no evidence to suggest that covalent bonding is involved. In addition, the inventors hypothesize that the surfactant utilized in accordance with the present invention may act to change the conformational nature of the polymer thus imparting the superior characteristics.

The hollow fiber membranes in accordance with the present invention have improved flux characteristics as discussed previously. The fiber surface may well be modified with surfactant so as to reduce inter and/or intra molecular surface tension and/or water wettability. This may enable the opening of previously closed pore structure helping to account for increased water flux across the membrane. When the treated fibers were examined under high magnification scanning electron microscopy (SEM), no apparent change in fiber structure was noted. Further, it also appears that the effective molecular size cutoff is numerically increased using the membranes of the present invention. For example, using bovine serum albumin (BSA) as a molecular marker (0.5 g/L), a BSA (in reverse osmosis water) rejection test showed a significant increase in the effective pore size for the surfactant treated fiber. A non-treated fiber, on the other hand, showed approximately 99% BSA rejection as opposed to treated fibers which showed a 70% rejection of BSA. The surfactant does not wash out of the fiber completely, even with repeated use and drying cycles.

The hydrophobic polymer and hydrophilic polymer are formed into a polymeric solution comprising an aprotic solvent. An aprotic solvent is a solvent which is not proton-releasing under processing conditions, i.e., having non-acidic or nonionizable hydrogen atoms. Preferably, this solvent is also soluble in water. A representative, non-limiting list of aprotic solvents useful in the invention includes dimethylformamide (DMF), dimethylsulfoxide (DMSO), dimethylacetamide (DMA), n-methylpyrrolidone and mixtures thereof. Preferably, the solvent is DMA. Depending on the desired property of the hollow fiber, a small amount of another solvent may be added instead of using a pure aprotic solvent. Preferably the additional solvent is a lower alcohol. This may enhance the precipitation of the polymer in the fiber formation.

Preferably, about 11–25 wt. %, more preferably, about 14–16 wt. %, and most preferably, about 15 wt. % of the fiber forming hydrophobic polymer are dissolved in the aprotic dimethylacetamide solvent. When less than about 11 wt. % of the hydrophobic polymer is used, the fibers formed are not strong enough to withstand the stresses involved in the high speed process of the present invention. On the other hand, when the level of hydrophobic polymer exceeds about 25 w. %, a fiber having inferior hydraulic properties is produced.

The hydrophilic polymer is dissolved in the solvent at a concentration of about 0.1–5 wt. %, more preferably, about 2–4 wt. %, and most preferably, about 3 wt. %. When the hydrophilic polymer is included in the dope solution above about 5 wt. %, the resulting fibers are stiff and difficult to manufacture. A similar result is seen when the amount of hydrophilic polymer is less than about 0.1 wt. %.

The polymeric solution has a viscosity of about 700–2300 cps, preferably about 1400–1700 cps, and most preferably, about 1500 cps at 25° C., as measured on a Brookfield viscometer. The solution is preferably filtered to remove any entrained particles (contaminants or undissolved components) to prevent apparatus blockage.

The polymeric solution is spun from the outer, annular orifice of a tube-in-orifice spinneret. A precipitating solution is delivered to the tube of the spinneret. The precipitating solution preferably includes a protic solvent, an aprotic solvent and water and combinations thereof. To some extent, the composition of the precipitating solution affects the porosity, clearance, tensile strength, wall thickness, inner and outer diameters and flux properties of the fiber. The practitioner of ordinary skill in the art will recognize that the precipitating solution compositions outlined in the following tables are helpful to direct the practitioner in selecting a useful formulation for a desired fiber end use. The selection of particular components and proportions is obviously up to the practitioner. The composition of the precipitating solution effective to produce a hollow fiber membrane for use in hemodialysis is illustrated below in Table IX.

TABLE IX

|  | Preferred | More Preferred | Most Preferred |
|---|---|---|---|
| Lower alcohol | 30–90 wt. % | 65–90 wt. % | 75–85 wt. % |
| Water | 10–35 wt. % | 10–35 wt. % | 10–35 wt. % |
| Aprotic Solvent | | | |

Precipitating solutions effective to produce a hollow fiber membrane for use in a hemofilter operation may comprise the components in proportions as illustrated in Table X.

TABLE X

|  | Preferred | More Preferred | Most Preferred |
|---|---|---|---|
| Lower alcohol | 30–90 wt. % | 50–85 wt. % | 80–85 wt. % |
| Water | 10–35 wt. % | 10–30 wt. % | 15–25 wt. % |
| Aprotic solvent | 0–50 wt. % | 5–35 wt. % | 10–20 wt. % |

Precipitating solutions effective to produce a hollow fiber membrane for use in a-blood filter to separate red blood cells from higher molecular weight materials may comprise the components in proportions as illustrated in Table XI.

TABLE XI

|  | Preferred | More Preferred | Most Preferred |
| --- | --- | --- | --- |
| Lower alcohol | 30–90 wt. % | 30–60 wt. % | 35–45 wt. % |
| Water | 10–35 wt. % | 10–30 wt. % | 15–25 wt. % |
| Aprotic solvent | 0–50 wt. % | 20–50 wt. % | 35–45 wt. % |

Precipitating solutions effective to produce a hollow fiber membrane for use in water filtration may comprise the components in proportions as illustrated in Table XII.

TABLE XII

|  | Preferred | More Preferred | Most Preferred |
| --- | --- | --- | --- |
| Lower alcohol | 30–98 wt. % | 30–60 wt. % | 35–45 wt. % |
| Water | 2–35 wt. % | 2–30 wt. % | 2–25 wt. % |
| Aprotic Solvent | 0–90 wt. % | 20–50 wt. % | 35–45 wt. % |

The above tables are merely offered to guide the practitioner in formulating fiber precipitation solutions. Indeed, the practitioner may decide that it is advantageous to operate in a "Preferred" range for one component while operating in a "Most Preferred" range for another.

Representative, non-limited examples of lower alcohols include methanol, ethanol, n-propanol, n-butanol, t-butyl alcohol, isopropanol, n-butanol, t-butyl alcohol, isobutyl alcohol or a mixture thereof. Preferably, the alcohol comprises methanol, ethanol, n-propanol, isopropanol, n-butanol or a mixture thereof. Various polyols, lower alcohols, glycerine etc. and/or aqueous solutions of inorganic salts may also be used. More preferably, the alcohol comprises isopropanol.

The water which may be used in the precipitating liquid may be tap water, deionized water or water which is a product of reverse osmosis. Preferably the water is deionized water which has first been treated by reverse osmosis.

The aprotic solvent used in the precipitating solution may again be dimethylformamide (DMF), dimethylsulfoxide (DMSO), dimethylacetamide (DMA), n-methylpyrrolidone and mixtures thereof. Preferably, the aprotic solvent is the same as that used in the polymeric fiber forming solution. Most preferably, the aprotic solvent is DMA.

The proportions of the alcohol, water and aprotic, solvent which make up the precipitating solution influence the morphology, clearance, permeability, selectivity, etc. of the hollow fiber membrane. It is generally preferred that the proportion of water in the precipitating solution remain relatively low, about 2 to 35 wt. %, to ensure that a fiber having desirable characteristics is produced. If the precipitating liquid contains less than about 2 wt. % water, the resultant: precipitation of the polymers may be too slow to form a fiber. On the other hand, a precipitating liquid that has a concentration of water greater than about 35 wt. % may result in a fiber having decrease flux with a small pore size.

As indicated above, the polymeric dope is pumped, filtered and directed to the outer, ring orifice of a tube-in-orifice spinneret. At the same time, the precipitating liquid is pumped to the inner coaxial tube of the spinneret. These two solutions are then delivered from the spinneret in a manner such that the polymer dope forms an annular sheath surround a flow of precipitating liquid within the annulus. Preferably, the spinneret head is maintained at a temperature of about 5°–85° C., more preferably, about 15°–25° C., and most preferably, about 18° C. The polymeric dope is subjected to a pressure of about 0–1400 kPa, more preferably, about 140–1000 kPa, and most preferably, about 350–850 kPa. In a preferred embodiment, the polymer dope is spun through a ring orifice having an outside diameter of about 0.018 to 0.040 inches (about 460 to 1.016 microns) and an inside diameter of about 0.008 to 0.010 inches (about 200 to 254 microns).

At the same time, precipitating liquid is pumped through the tube of the spinneret at a pressure of about 0–1000 kPa, preferably about 0–100 kPa, and most preferably, about 1–20 kPa. In a preferred embodiment, the precipitating liquid or diluent solution is delivered through a tube having an outside diameter of substantially about 0.010 inches (about 254 microns) and an inside diameter of substantially about 0.005 inches (about 127 microns).

In a preferred embodiment, in order to produce a hollow fiber having an approximately 380 micron outside diameter and an approximately 280 micron inside diameter, the polymer dope is delivered to the spinneret at a rate of substantially about 1.0–10 mL/min, more preferably, about 2–5 mL/min, most preferably, about 3 mL/min, and the precipitating liquid is delivered at a rate of at least about 1.0–10 mL/min, more preferably, about 2–5 mL/min, and most preferably, about 2–3 mL/min. The spinneret is oriented in a manner such that fiber production is driven by fluid flow and by removal from the spinneret by gravity effects. Preferably, the fiber emerges from the spinneret and is pulled by gravity and the take-up speed in a nearly vertical direction downwards., In order to provide satisfactory fibers in the practice of the invention, laminar fluid flow should be maintained both within the spinneret head and the spun fluids which interact to precipitate the fiber. If turbulent flow is present in the spinneret head, especially within the channels which convey the polymeric dope, gas pockets may develop and ultimately form large voids in the spun fiber. Turbulent flow within the spun fluids may also result in voids within the fiber.

It is helpful to visualize the spinneret dimensions by resort to ratios of the annular orifice for passage of the polymeric dope and the coaxial tubular orifice for passage of the diluent or precipitating solution. One helpful ratio is the ratio of the cross-sectional area of the annular orifice to tubular orifice. Preferably, the ratio is greater than about 1:1, more preferably, the ratio is about 2:1 to 5:1, and most preferably, the ratio of the annular orifice to tubular orifice cross-sectional area is about 3:1 to 4:1. Another helpful dimensional ratio is the annular ring thickness to tube inside diameter. Preferably, the ratio is greater than about 1:1, more preferably, the ratio is about 2:1 to 7:1, and most preferably, the ratio of the annular ring thickness to tube inside diameter is about 3:1 to 6:1. A third helpful dimensional ratio is the outside diameter of the annular orifice to tube inside diameter. Preferably, this ratio is greater than about 2:1, more preferably, the ratio is about 3:1 to 10:1, and most preferably, the ratio of the annular outside diameter to tube inside diameter is about 5:1 to 8:1.

As the fiber emerges from the spinneret, it drops in a substantially downward vertical direction over a distance of about 0.1–10 m, more preferably, about 0.5 to 2.0 m, and most preferably, about 1.0 to 1.5 m. This allows the precipitating liquid to substantially precipitate the polymer in the annular dope solution forming the solid fiber capillary before it is immersed in a quenching solution. Between the spinneret and the quenching bath, the fiber drops through the atmosphere, air, air with a particular relative humidity, an augmented atmosphere, e.g., a mixture of air or air with a particular relative humidity and a gas, an inert gas, or a mixture thereof. Preferably, for ease in processing and to produce a high quality fiber, the fiber drops through air maintained at a temperature of 0° C. to 100° C., more preferably, the air is maintained at a temperature of 5° C. to 50° C. and most preferably at 15° C. to 25° C. Preferably the air is also maintained at a relative humidity of substantially about 10% to 90%, more preferably from substantially about 20% to 80% and most preferably from substantially about 40% to 65%. This gaseous atmosphere may be relatively stagnant, or there can be fluid flow. Preferably, the flow rate is sufficient to allow complete air change over in the spinning environment once every 30 minutes. In one preferred embodiment, the gas flow is about 10 L/min.

Next, the fiber is submerged in a tank comprising water and 0-10 wt. % other materials. Again, the water may be tap, deionized water, or the product of a reverse osmosis process. The temperature of the quenching bath is preferably between about 0° to 100° C., more preferably, about 15° C. to 45° C., and most preferably, about 35° C. The water temperature directly affects the performance of the fiber. Lower temperatures can reduce the flux of the resulting fiber. Increasing the quenching bath temperature can increase the flux of the fiber.

The fiber is preferably immersed in the quenching bath for a period of about 0.1 to 10 seconds, preferably about 0.1 to 5 seconds, and most preferably, about 1 second. This residence time permits the full precipitation of the hydrophobic polymer to form the microporous hollow fiber. The quenching bath also helps to remove the excess, unprecipitated polymers as well as some of the hydrophilic polymer, the water soluble solvent and precipitating liquid.

After the quenching bath, the fiber may be further rinsed to remove additional unprecipitated polymers and solvents. This rinsing may be accomplished in a water bath arrangement. Preferably, the additional rinse is achieved in a water bath having a water temperature of about 0° C.-100° C., more preferably, about 15° C.-45° C., and most preferably, about 35° C. The fiber is then wound on a take-up reel. The take-up reel is preferably rotating at; a speed such that the fiber is being wound at about 90-150% of the rate at which it is being formed at the spinneret. More preferably, the fiber is being wound at a rate substantially equal to that at which it is being produced. In other words, the fiber is taken up with enough speed (i) to create a fiber of the desired size and (ii) to apply sufficient tension to the fiber such that it will remain taut in the take-up guide unaffected by ambient air currents, i.e. there is no "draft."

The surfactant may be incorporated into or onto the hollow fiber membrane through a number of mechanisms. The polymeric spinning solution itself may comprise about 0.01 to 10 wt. % of surfactant. In other useful embodiments, about 0.01 to 10 wt. % of a surfactant may be incorporated into the quenching bath, rinse bath, take-up reel bath, a surfactant bath or any other process step wherein the gelled tube or precipitated hollow fiber is contacted with an aqueous or organic solution, or both. In a preferred embodiment, the fiber is cut and formed into bundles that are then soaked in a surfactant solution.

Preferably, the hollow fiber membrane or gelled polymeric solution has a contact time with a surfactant solution of less than about 10 seconds. If the surfactant is incorporated into the quenching bath, rinse bath or take-up reel bath, the fiber's residence time in the solution is about 4 to 48 hours. In another embodiment, the fibers are cut and bundled prior to soaking in the surfactant solution for less than 72 hours, more preferably for less than 30 hours and most preferably for less than 24 hours.

The surfactant solution may be contacted with the gelled polymer or polymeric precipitate at a temperature of about 0° C. to 100° C. More preferably, the hollow fiber or polymeric precipitate is contacted with a surfactant solution at a temperature of about 20° C. to 50° C., and most preferably at about 40° C. to 50° C.

The hollow fibers may then be dried by any method appropriate to general manufacturing procedures including but not limited to air, heat, vacuum, or any combination thereof. The hollow fibers may be further processed to form useful articles including hemodialyzer cartridges, hemofilters, blood filters, water filters, etc., having improved performance levels.

Again, in a preferred embodiment of the present invention, the hollow fibers 28 formed may be cut into bundles (not shown) of a constant length and soaked in an aqueous surfactant solution (not shown) as discussed above.

Water flux is determined by a test developed in-house. Specifically, the water flux is measured on test mat size (0.02 to 0.08 $m^2$) bundles which are potted in a polycarbonate cylindrical case. A transmembrane pressure of 5 psi is maintained across the unit as reverse osmosis water is pumped through one of two side ports (one side port clamped off), exiting out one of two end ports (one end port clamped off). The water is collected via graduated cylinder on a timed basis to determine flux. Drying of the membrane may be accomplished by circulating dry air through and around the hollow fiber membranes. The flux of a fiber which has been cycled in this manner can be compared to its original values to determine the membrane's rewettability. The process is repeated in duplicate to insure reproducibility.

EXAMPLES

The following specific examples which contain the best mode, can be used to further illustrate the invention. These examples are merely illustrative of the invention and do not limit its scope.

Example 17

A polymer solution was prepared by dissolving 15.1% by weight of a polysulfone polymer having a molecular weight of about 60,000 to 65,000 and 2.8% by weight of PVP having a K-value of about 80 to 87 in 81.6% dimethylacetomide with 0.5% by weight of an exthoxylated (15 EO) cocoamine surfactant. The material was filtered and then pumped into a tube-in orifice spinneret at a rate of 3.5-3.7 ml/min at a temperature of about 65°-72° F.

A diluent solution containing 40% by weight isopropanol, 40% by weight DMAC and 20% by weight deionized, reverse osmosis water was delivered to the spinneret at a temperature of 65°-72° F and at a rate of 2.5-2.6 ml/min. The polymeric dope solution was delivered through the outer, annular orifice of the spinneret having an outside dimension of about 0.037 inches and an inside dimension of about 0.010 inches. The diluent was delivered through a tube orifice within the annular orifice having an inside diameter of about 0.005 inches. The spinneret head was maintained at about 70° F. by means of a water bath or run without a water bath and maintained at room temperatures 68°-74° F. The spinneret discharged the column of dope solution downward through air at a temperature of 68°-80° F. and relative humidities of 20-60%. The fiber dropped through this controlled environment 1.1 meters into a reverse osmosis quenching water bath which was maintained constant at 90°-100° F. Reverse osmosis water was pumped into the quenching bath resulting in overflow. The fiber was pulled at approximately 10 RPM into a second bath containing reverse osmosis water maintained at a temperature of 90°-100° F.

The fiber was removed from the take-up wheel, cut and formed into bundles containing approximately 2,100 fibers of about 30.5 cm. The fiber bundles were soaked in reverse osmosis water with overflow maintained at 46°–58° C. The bundles were centrifuged and dried at 38°–50° C. in a convection oven.

Example 18

A polymer solution was prepared by dissolving 16.2% by weight of a polysulfone polymer having a molecular weight of about 60,000 to 65,000 and 2.8% by weight of PVP having a K-value of about 80 to 87 in 81.6% dimethylacetomide with 0.5% by weight of an ethoxylated (15 EO) cocoamine surfactant. The material was filtered and then pumped into a tube-in orifice spinneret as in Example 17.

A diluent solution containing 98% by weight isopropanol, 0% by weight DMAC and 2% by weight deionized, reverse osmosis water was delivered to the spinneret at a temperature of 65°–72° F. and at a rate of 2.8–3.0 ml/min. The polymeric dope solution was delivered through the outer, annular orifice of the spinneret having an outside dimension of about 0.037 inches and an inside dimension of about 0.010 inches. The diluent was delivered through a tube orifice within the annular orifice having an inside diameter of about 0.005 inches. The spinneret head was maintained at about 70° F. by means of a water bath or run without a water bath and maintained at room temperatures 68°–74° F. The spinneret discharged the column of dope solution and diluent downward through air at a temperature of 68°–80° F. and relative humidities of 20–60%. The fiber dropped through this controlled environment 1.1 meters into a reverse osmosis quenching water bath which was maintained constant at 90°–100° F. Reverse osmosis water was pumped into the quenching bath resulting in overflow. The fiber was pulled at approximately 10 RPM into a second bath containing reverse osmosis water maintained at a temperature of 90°–100° F.

The fiber was removed from the take-up wheel, cut and formed into bundles containing approximately 2,100 fibers of about 30.5 cm. The fiber bundles were soaked in reverse osmosis water with overflow maintained at 46°–58° C. The bundles were centrifuged and dried at 38°–50° C. in a convection oven.

Example 19

A polymer solution was prepared by dissolving 15.1% by weight of a polysulfone polymer having a molecular weight of about 60,000 to 65,000 and 2.8% by weight of PVP having a K-value of about 80 to 87 in 82.1% dimethylacetomide. The material is filtered and then pumped into a tube-in orifice spinneret at a rate of 3.5–3.7 ml/min at a temperature of about 65°–72° F.

A diluent solution containing 80% by weight isopropanol, 0% by weight DMAC and 20% by weight deionized, reverse osmosis water was delivered to the spinneret at a temperature of 65°–72° F. and at a rate of 2.5–2.6 ml/min. The polymeric dope solution was delivered through the outer, annular orifice of the spinneret having an outside dimension of about 0.020 inches and an inside dimension of about 0.010 inches. The diluent was delivered through a tube orifice within the annular orifice having an inside diameter of about 0.005 inches. The spinneret head was maintained at about 70° F. by means of a water bath or run without a water bath and maintained at room temperatures 68°–74° F. The spinneret discharged the column of dope solution and diluent downward through air at a temperature of 68°–80° F. and relative humidities of 20–60%. The fiber dropped through this controlled environment 1.5 meters into a reverse osmosis quenching water bath which was maintained constant at 90°–00° F. Reverse osmosis water was pumped into the quenching bath resulting in overflow. The fiber was pulled at approximately 20 RPM into a second bath of reverse osmosis water maintained at a temperature of 90°–100° F.

The fiber was removed from the take-up wheel, cut and formed into bundles containing approximately 6,000 fibers of about 30.5 cm. The fibers were then placed for 24 hours in a static soak tank containing 1% by weight of an ethoxylated (15 EO) cocoamine surfactant and water maintained at 68° F. to 100° F. The bundles were centrifuged and dried at 38°–50° C. in a convection oven.

Example 20

A polymer solution was prepared by dissolving 15.1% by weight of a polysulfone polymer having a molecular weight of about 60,000 to 65,000 and 2.8% by weight of PVP having a K-value of about 80 to 87 in 82.1% dimethylacetomide. The material is filtered and then pumped into a tube-in orifice spinneret at a rate of 3.5–3.7 ml/min at a temperature of about 65°–72° F.

A diluent solution containing 90% by weight isopropanol, 0% by weight DMAC and 10% by weight deionized, reverse osmosis water was delivered to the spinneret at a temperature of 65°–72° F. and at a rate of 2.5–2.6 ml/min. The polymeric dope solution was delivered through the outer, annular orifice of the spinneret having an outside dimension of about 0.020 inches and an inside dimension of about 0.010 inches. The diluent was delivered through a tube orifice within the annular orifice having an inside diameter of about 0.005 inches. The spinneret head was maintained at about 70° F. by means of a water bath or run without a water bath and maintained at room temperatures 68°74° F. The spinneret discharged the column of dope solution and diluent downward through air at a temperature of 68°–80° F. and relative humidities of 20–60%. The fiber dropped through this controlled environment 1.5 meters into a reverse osmosis quenching water bath which was maintained constant at 90°–100° F. Reverse osmosis water was pumped into the quenching bath resulting in overflow. The fiber was pulled at approximately 110% of the rate at which it is being formed into a second bath containing 1% by weight of an ethoxylated (15 EO) cocoamine surfactant and reverse osmosis water maintained at a temperature of 90°–100° F.

The fiber was removed from the take-up wheel, cut and formed into bundles containing approximately 6,000 fibers of about 30.5 cm. The bundles were centrifuged and dried at 38°–50° C. in a convection oven.

Example 21

A polymer solution was prepared by dissolving 15.1% by weight of a polysulfone polymer having a molecular weight of about 60,000 to 65,000 and 2.8% by weight of PVP having a K-value of about 80 to 87 in 82.1% dimethylacetomide. The material is filtered and then pumped into a tube-in orifice spinneret at a rate of 3.5–3.7 ml/min at a temperature of about 65°–72° F.

A diluent solution containing 90% by weight isopropanol, 0% by weight DMAC and 10% by weight deionized, reverse osmosis water was delivered to the spinneret at a temperature of 65°–72° F. and at a rate of 2.5–2.6 ml/min. The polymeric dope solution was delivered through the outer, annular orifice of the spinneret having an outside dimension of about 0.020 inches and an inside dimension of about 0.010 inches. The diluent was delivered through a tube orifice within the annular orifice having an inside diameter of about 0.005 inches. The spinneret head was maintained at about 70° F. by means of a water bath or run without a water bath and maintained at room temperatures 68°–74° F. The spinneret discharged the column of dope solution and diluent downward through air at a temperature of 68°–80° F. and relative humidities of 20–60%. The fiber dropped through this controlled environment 1.5 meters into a reverse osmosis quenching water bath which was maintained constant at 90°–100° F. Reverse osmosis water was pumped into the quenching bath resulting in overflow. The fiber was pulled at approximately 20 RPM into a second bath containing 1% by weight of an ethoxylated (2 EO) cocoamine surfactant and reverse osmosis water maintained at a temperature of 90°–100° F.

The fiber was removed from the take-up wheel, cut and formed into bundles containing approximately 6,000 fibers of about 30.5 cm. The bundles were centrifuged and dried at 38°–50° C. in a convection oven.

Test Data

The membranes made from the examples above were measured for flux, rewettability and diffusional flow rates. The water flux was measured on test mat size (0.02 to 0.08 $m^2$) bundles which were potted in a polycarbonate cylindrical case. A transmembrane pressure of 5 psi was maintained across the unit as reverse osmosis water was pumped through one of two side ports (one side port clamped off), exiting out one of two end ports (one end port clamped off). The water was collected via graduated cylinder on a timed basis to determine flux. Drying of the membrane was accomplished by circulating dry air through and around the hollow fiber membranes. The flux of fibers cycled in this manner were compared to their original values to determine the membrane's flux and rewettability characteristics.

The hollow fiber membranes were also tested for diffusional air flow, a method of determining the integrity of a membrane. When dry, air flow easily through the pores in the membrane; when wet, air does not flow through an intact membrane. Membranes were wet with reverse osmosis water to fill the pores. A transmembrane pressure equal to 30 psi was applied to the upstream side of the membrane. Air which diffuses through is measured to determine the integrity of the membrane.

Test Data #1

A filter module comprising approximately 1.4 $m^2$ of membrane prepared in accordance with Example 17 was tested in accordance with the previously disclosed flux test. The module produced a water flux of 0.0026 mL/min/mmHg/$cm^2$. The module also produced a diffusional air flow of 20 mL/min at 30 psi inlet air pressure.

Test Data #2

A filter module comprising approximately 1.4 $m^2$ of membrane fabricated in accordance with Example 18 was tested for its ability to rewet upon successive dryings. Each wet dry cycle trial consisted of the following steps:

1) flux test
2) diffusional flow
3) air dried by blowing 20° C. air through the lumen for 24 hours The results are tabulated below:

|         | Flux   | Diff. Flow |
|---------|--------|------------|
| Trial 1 | 0.0020 | 21         |
| Trial 2 | 0.0030 | 27         |
| Trial 3 | 0.0034 | 29         |
| Trial 4 | 0.0036 | 39         |

Test Data #3

A filter module comprising approximately 1.4 $m^2$ of membrane fabricated in accordance with Example 19 was tested for its rewetting characteristics and its ability to remove bovine serum albumin from blood. Each rewetting test trial consisted of the following steps:

1) flux test
2) air dried by flowing 20° C. air through the lumen for 24 hours
3) rewet The results are tabulated below:

|         | Flux     |
|---------|----------|
| Trial 1 | 0.000428 |
| Trial 2 | 0.000446 |
| Trial 3 | 0.000457 |
| Trial 4 | 0.000454 |
| Trial 5 | 0.000476 |

The bovine serum albumin rejection rate was 80%.

Test Data #4

A filter module comprising approximately 3.0 $m^2$ of membrane fabricated in accordance with Example 20 was tested for its initial flux rate and diffusional flow characteristics. The module produced a water flux of 0.00146 and a diffusional air flow of 53 mL/min.

Test Data #5

A filter module comprising approximately 3.0 $m^2$ of membrane fabricated in accordance with Example 21 was tested for its initial flux rate and diffusional flow characteristics. The module produced a water flux of 0.00092 and a diffusional air flow of 51 mL/min.

C. Asymmetric, Microporous, Hollow Fiber Membrane Incorporating a Polyimide. The third embodiment of the present invention is directed to an asymmetrical microporous, hollow fiber membrane that includes a polyimide polymer that is highly polar. The membrane is particularly well suited for medical applications where the membrane will come into contact with blood because it is biocompatible, does not activate complement, and has the remarkable ability to exhibit high sieving coefficients for middle molecules such as $\beta_2$ microglobulins and myoglobins. When used as a membrane for dialysis applications, the membrane has a pore size ranging from substantially about 0.001 µm to substantially about 0.01µm with the average pore size being from substantially about 0.003 µm to substantially about 0.005 µm.

Also surprisingly, the membrane is equally suited in all filtration applications for its unique ability to completely remove existing endotoxin from the solution being filtered.

When this unique membrane is used as a water filter, the pore size preferably ranges from about 0.005 µm to about 0.5

μm with an average pore size of from about 0.05 μm to about 0.1 μm. When used as a plasma filtration membrane the maximum pore size ranges from substantially about 0.1 μm to substantially about 0.2 μm The highly polar polymer in accordance with the present invention is preferably an aromatic polyimide that when precipitated as a membrane is immediately wettable without the use of polymer additives or surfactants. The preferred polyimide in accordance with the present invention is disclosed in U.S. Pat. No. 3,708,458 to Alberino which is hereby incorporated by reference. The polyimide is prepared from benzophenone-3,3',4,4'-tetracarboxylic acid dianhydride and a mixture of 4,4'-methylenebis(phenyl isocyanate) and toluene diisocyanate (2,4- or 2,6-isomer) of-mixtures thereof. The polyimide includes the recurring group:

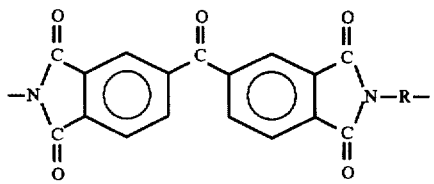

wherein 10% to 90% of the R groups are

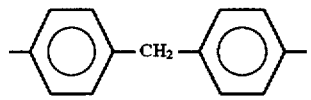

and the remaining R groups include either

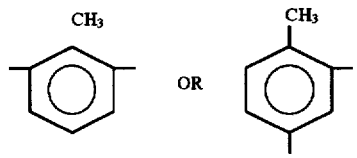

The aromatic iso- and diisocyanates may be substituted by their amine analogs. The CAS Registry No. of the preferred polyimide is 58698-66-1. The polyimide is available from Lenzing Corp.(Austria) under the P-84 and/or HP P-84 (high purity) marks. In an alternative embodiment, a polymer based on the phenyl-indane diamine; 5(6)-amino-1-(4'-aminophenyl)-1,3-trimethylindane with a CAS Registry No. of 62929-02-6 may be used. The alternative embodiment polymer is available from Ciba-Geigy Corporation (Hawthorne, N.Y.) under the "Matrimid 5218" mark.

The structure of the polymer repeating unit is believed to consist of:

The alternative preferred embodiment may be prepared by the methods disclosed in U.S. Pat. No. 3,856,752.

The polyimide polymers useful in accordance with the present invention preferably have a molecular weight of about 30,000 to 125,000 daltons. More preferably, the molecular weight is about 35,000 to 115,000 daltons and most preferably, the molecular weight is about 40,000 to 105,000 daltons.

As stated previously, no additional additives, such as polyvinylpyrrolidone, polyethylene glycol, glycerine, cellulose or starch derivatives or amphoteric, zwitterionic, nonionic, anionic, or cationic surfactants, are needed to produce a hollow fiber membrane that wets immediately upon contact with blood, water and other aqueous solutions and maintains the rewettability for at least 6-7 sterilizations by steam or chemicals. Because no additional polymers are needed to make the resultant fiber wettable, the choice of solvents for use as the precipitating solution is critical in influencing the hydrophilicity, structure and porosity of the fiber. In addition, the elimination of additives in the polymeric dope solution decreases and virtually eliminates all but trace amounts of solids and/or oxidizable material that is leachable from the resultant fiber. Further, the structural integrity of the resultant hollow fiber membrane is more stable after the removal of the solvent and/or antisolvents and nonsolvents.

Initially, the polyimide polymer is dissolved in a solvent. Preferably, this solvent is also miscible with water. A representative, non-limiting list of solvents useful in the invention includes dimethylformamide (DMF), dimethylsulfoxide (DMSO), dimethylacetamide (DMA), n-methylpyrrolidone, and mixtures thereof. Preferably, the solvent is DMF, an aprotic solvent. Depending on the desired properties of the hollow fiber, a small amount of an antisolvent may be added in small quantities to the primary solvent that is used. The addition of an antisolvent in the polymer forming solution will enhance the desired precipitate characteristics of the polymer during fiber formation. For example, adding acetic acid in the amount of 4-7 wt. % ensures that the fiber has a uniform sponge-like structure, free of voids, large vacuous spaces extending from the inner membrane wall to the outer membrane wall that can permit the passage of large molecular weight molecules if the void pierces the inner and/or outer membrane wall. Alternatively, additional amounts of solids may be added to the polymer solution up to 25.0 wt. % to solve this problem. The homogeneous, sponge-like structure may also be achieved in accordance with the process and formulations described herein.

Figure 4A:
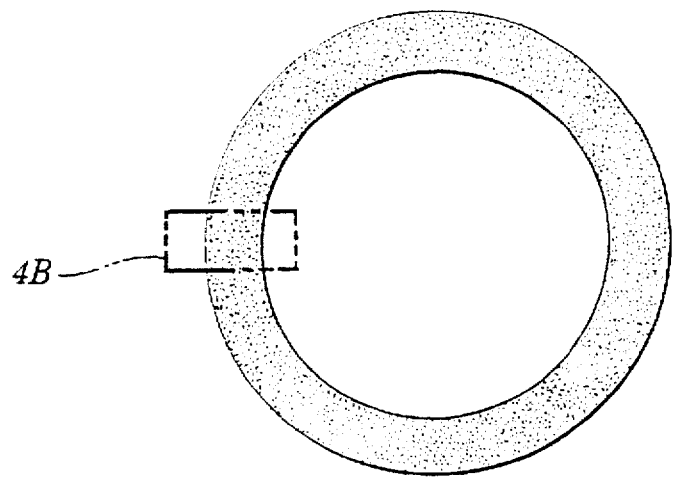
FIG. 4A is an enlarged, microscopic, cross-sectional view of the hollow fiber membrane incorporating a polyimide in accordance with the present invention illustrating the "homogeneous sponge-like" structure.
Figure 4B:
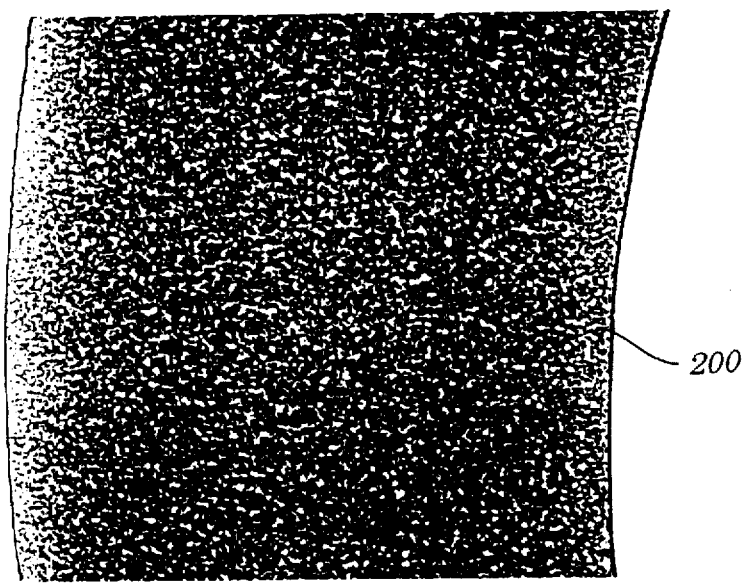
FIG. 4B is a greatly enlarged view thereof taken from the area enclosed by box 4B in FIG. 4A.

FIG. 4A depicts a cross section of a hollow fiber membrane in accordance with the present invention magnified 130× taken on a Hitachi S-800 scanning electron microscope. FIG. 4B which is a 10× magnification (1300×) of the

Figure 5:
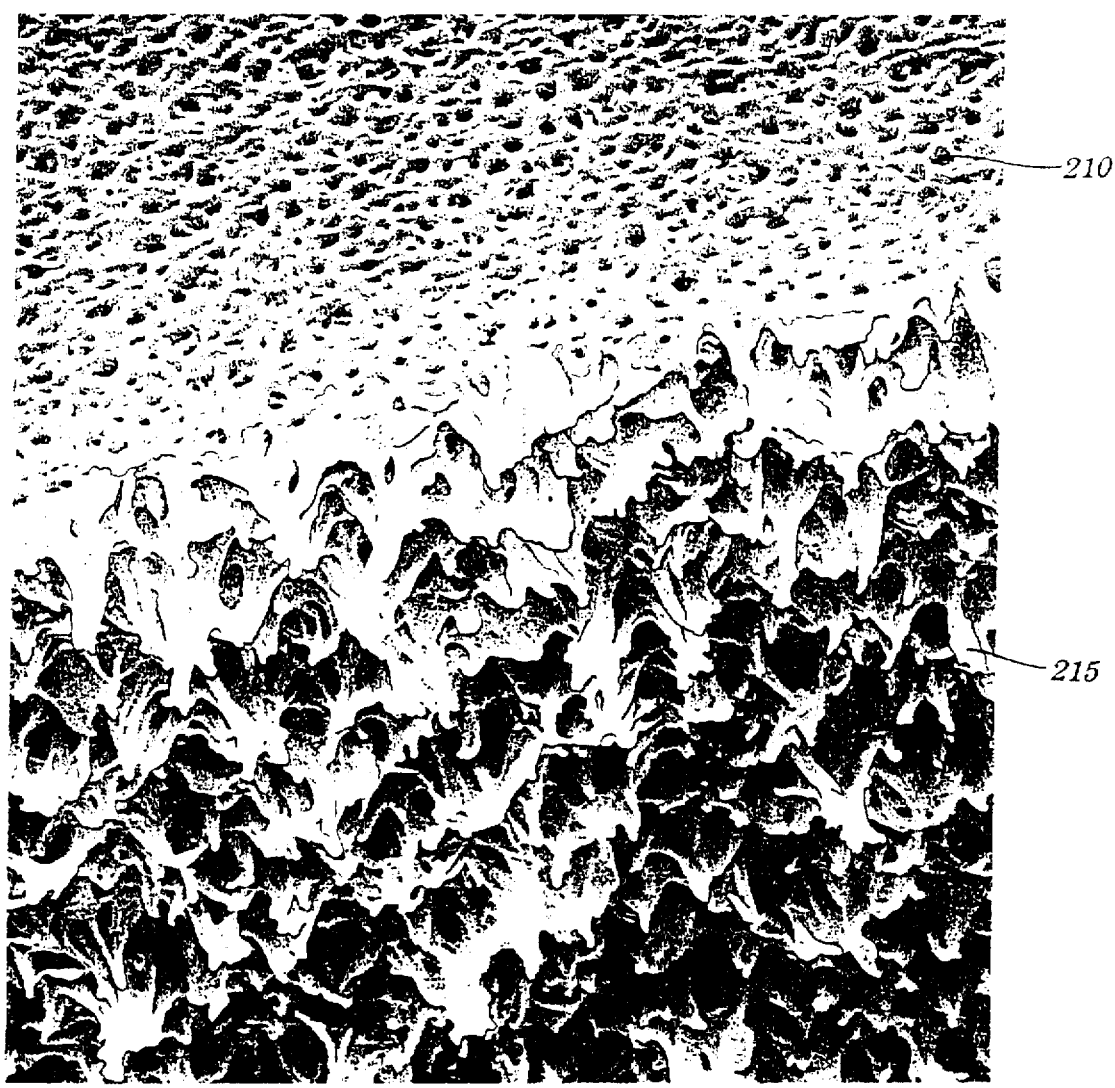
FIG. 5 is an enlarged detailed view of the hollow fiber membrane incorporating a polyimide in accordance with the present invention illustrating the homogenous sponge-like structure taken at a 45° angle of cross-section.
Figure 6A:
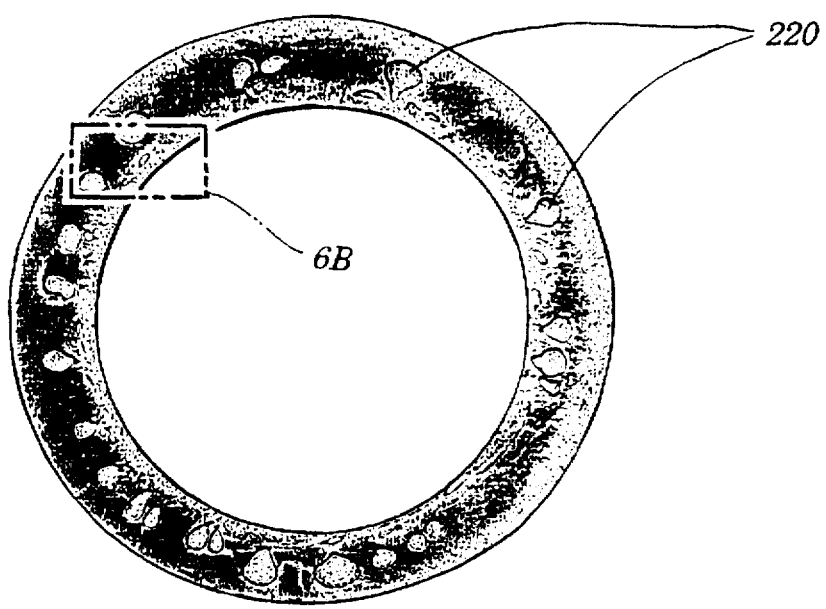
FIG. 6A is an enlarged, microscopic cross-sectional view of prior art hollow fiber membranes illustrating "voids"
Figure 6B:
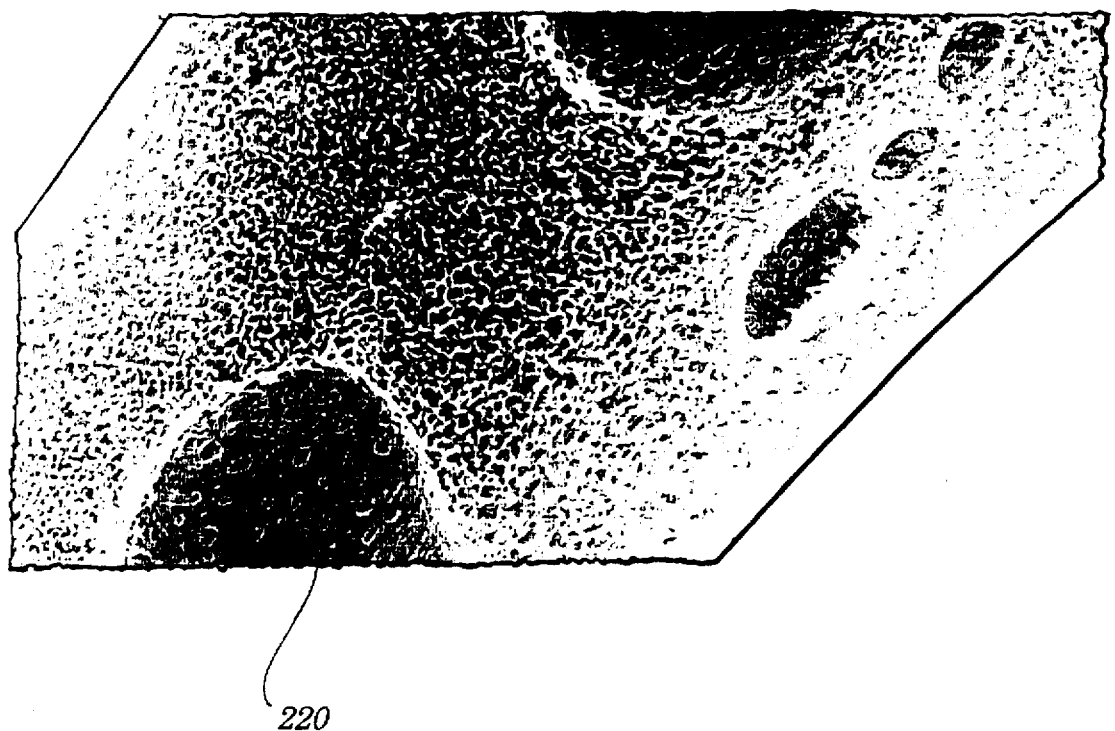
FIG. 6B is a greatly enlarged detail view thereof taken from the area enclosed by box 6B in FIG. 6A.

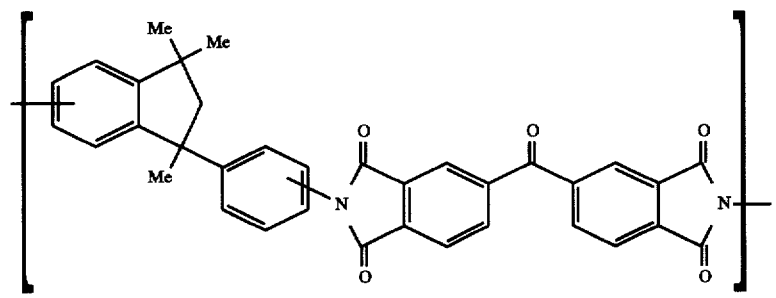

area enclosed by box 4B in FIG. 4A and illustrates the "uniform sponge-like structure" 200 of hollow fiber membranes in accordance with the present invention. FIG. 5 is a 10,000× view taken at a 45° angle of cross-section of hollow fibers in accordance with the present invention showing the outer membrane wall 210 and the sponge-like inner composition 215. "Voids" 220, which characterize many hollow fiber membranes, may be seen by referring to FIGS. 6A (130×) and 6B (1300×). The absence of voids in the formed hollow fiber membrane results in a mechanically stronger fiber with enhanced diffusion rates.

Preferably, about 15–25 wt-%, more preferably, about 16–20 wt-%, and most preferably, about 17–19 wt-% of the fiber forming polyimide polymer is dissolved in the dimethylformamide solvent. When less than 15 wt-% of the polyimide polymer is used, the fibers formed may not be strong enough to withstand the stresses involved in the high speed process in accordance with the method of the present invention. In addition, test data regarding sieving and clearance characteristics are not reproducible because the fibers lack the desirable uniform sponge-like structure. Further, the fibers lack integrity due to the weakness from the voids in the fiber walls.

Higher polyimide solids may be employed in organic solvent systems if spinneret housings, feed lines, and polymer solution tanks are heated. Upon heating, the viscosity of the polymer solution is lowered, allowing otherwise unusable polymer solution formulations to be spun. Depending upon the composition of the precipitating solution the skilled practitioner chooses, heating and/or cooling the system may influence the morphology and performance characteristics of the resultant fiber membrane.

The polymeric solution has a viscosity of about 1500–5000 cps, preferably about 2000–4000 cps, and most preferably about 3500–3800 cps at 25° C., as measured on a Brookfield (LV) viscometer. The solution is preferably filtered to remove any entrained particles (contaminants or undissolved components) to prevent apparatus blockage.

The polymeric solution is spun from the outer, annular orifice of a tube-in orifice spinneret. A precipitating solution is delivered to the tube of the spinneret. The precipitating solution includes a solvent with respect to the polymer and a non-solvent with respect to the polymer or a variety of non-solvents. The composition of the precipitating solution is critical because it affects the porosity, degree of uniform sponge-like structure, clearance, tensile strength, wall thickness, inner and outer diameters and flux properties of the fiber.

Figure 7:
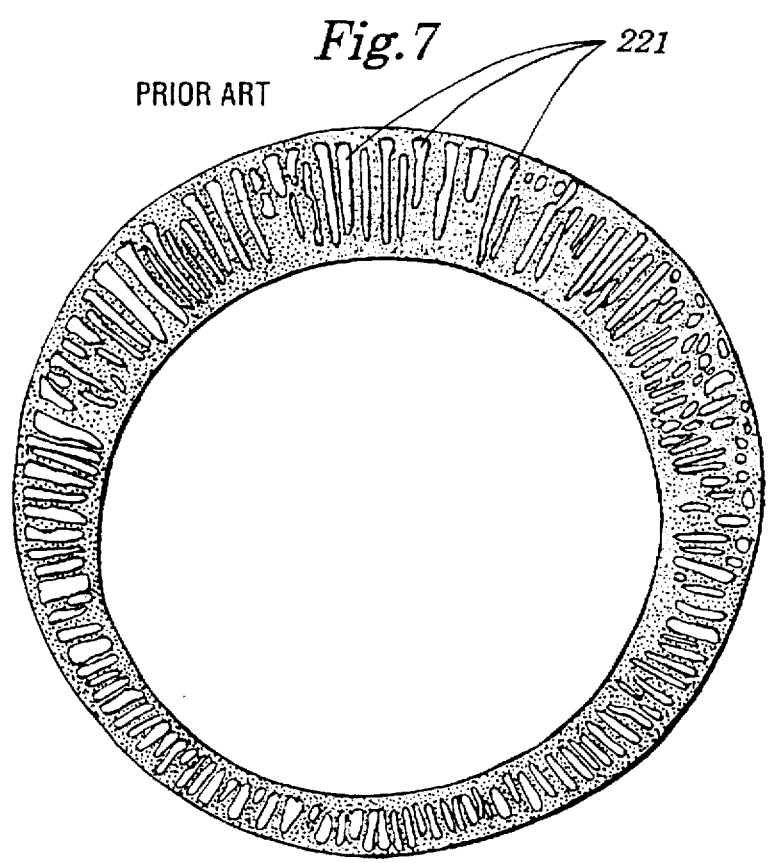
FIG. 7 is an enlarged, microscopic cross-sectional view of hollow fiber membranes with voids.

For example, as the weight percent of the solvent with respect to the polymer increases, fiber formation is impaired and is characterized by a "glassy"0 weaker structure and it becomes increasingly difficult to "pull" the fiber. Conversely, as the weight percent of the solvent with respect to the polymer decreases and the weight percent of water and/or other non-solvents with respect to the polymer increases, voids are seen in the fiber structure which may allow high molecular weight molecules to pass through the fiber if they pierce the outer membrane wall. This may best be seen in FIG. 7 which illustrates a fiber cross-section magnified 130× with voids 221 that resulted from using a precipitating solution with an increased weight percent of non-solvent with respect to the polymer. In addition, as the weight percent of water and/or other non-solvents with respect to the polymer increases, a low pore density on the outer fiber wall and a tighter closed inner wall with a low flux is seen. It will therefore be appreciates by those skilled in the art that the selection of the composition of the precipitating solution is crucial.

The composition of the precipitating solution effective to produce a hollow fiber membrane for use in hemodialysis, as well as, water filters, autologous blood filters, and plasma filters is illustrated below in Table XIII.

TABLE XIII

|  | Preferred | More Preferred | Most Preferred |
| --- | --- | --- | --- |
| Solvent with respect to polymer | 50–99 wt. % | 60–95 wt. % | 75–90 wt. % |
| Water | 35–1 wt. % | 30–5 wt. % | 20–10 wt. % |
| Add'l Non-Solvents with respect to polymer | 15–0 wt. % | 10–0 wt. % | 5–0 wt. % |

The table above is merely offered to guide the practitioner in formulating precipitating solution solutions. Indeed, the practitioner may decide that it is advantageous to operate in a "Preferred" range for one component while operating in a "Most Preferred" range for another. In addition, depending on which formulation of precipitating solution the practitioner selects, he or she may also vary the percent solids in the polymer solution to obtain a fiber of the desired characteristics.

The water which may be used in the precipitating solution may be tap water, deionized water or water which is a product of reverse osmosis. Preferably the water has first been treated by reverse osmosis.

As stated previously, the solvent (with respect to the polymer) used in the precipitating solution is dimethylformamide (DMF), dimethylsulfoxide (DMSO), dimethylacetamide (Dan), n-methylpyrrolidone and mixtures thereof. Preferably, the solvent is the same as that used in the polymeric fiber forming solution. More preferably, the solvent is DMA or DMF. Most preferably, the solvent is DMF.

Additional combinations of solvents and non-solvents, which may or may not contain salts, may be used so long as they are miscible with dimethylformamide, dimethylsulfoxide, dimethylacetamide, n-methylpyrrolidone and mixtures thereof. A representative, non-limiting list of non-solvents (with respect to the polymer) that may be used in the precipitating solution are acetic acid, isopropanol, water, glycerol, acetic anhydride, and ethanol.

The proportions of the water, and other non-solvents (e.g. alcohol) which may make up the precipitating solution influence the morphology, clearance, permeability, and selectivity characteristics of the hollow fiber membrane. In particular, the total absence of a solvent with respect to the polymer in the precipitating solution may result in a small number of pores in the fiber wall as well as lower flux. Further, water is clearly an important ingredient in the precipitating solution used in this membrane formation process.

Because the addition of water affects the performance characteristics of the resultant fiber membrane it is generally preferred that the proportion of water in the precipitating solution be about 1–35 wt. %, to ensure proper fiber performance characteristics. Less than about 10 wt. % of water may result in the polymeric solution precipitating too slowly forming a fiber with increased pore size. This is desirable to form a fiber for use in water filters but would not, for example, form a fiber suitable for use as a dialyzer fiber. Conversely, a concentration of water greater than about 35 wt. % results in a fiber with lower pore density on the outside and a tighter closed inner wall with a general decrease in flux. However, when the proportion of water falls within 1–35 wt. %, we see enhanced uniformity in the desirable sponge-like structure and the hollow fiber membrane is characterized by the complete absence of voids. This uniformity results in more overall uniform flux with respect to all types of filters and tighter controls with respect to molecular cutoffs in dialyzer applications.

Initially, the highly polar polymer is diluted in DMF. Depending on the desired properties and characteristics of the hollow fiber, a small amount of a non-solvent (with respect to the polymer) (also called anti-solvents) other than water may be added instead of using pure DMF solvent. This may enhance the precipitation of the polymer in the fiber formation. For example, the addition of 4–7 wt. % glacial acetic acid to the polymer/DMF solution enhances the uniform sponge-like structure of the resultant fiber and the fiber is further characterized by the complete absence of voids.

The polymeric dope solution is pumped, filtered and directed to the outer, ring orifice of a tube-in-orifice spinneret. At the same time, the precipitating solution is pumped to the inner coaxial tube of the spinneret. These two solutions are then delivered from the spinneret in a manner such that the polymer dope forms an annular sheath surround a flow of precipitating solution within the annulus. Preferably, the spinneret head is maintained at a temperature of about 5°–85° C., more preferably, about 15°–25° C., and most preferably, about 22° C. The polymeric dope is subjected to a pressure of about 0–1400 kPa, more preferably, about 140–1000 kPa, and most preferably, about 350–850 kPa. In a preferred embodiment, the polymer dope is spun through a ring orifice having an outside diameter of about 0.018 to 0.040 inches (about 460 to 1,016 microns) and an inside diameter of about 0.008 to 0.010 inches (about 200 to 280 microns).

At the same time, precipitating solution is pumped through the tube of the spinneret at a pressure of about 0–1000 kPa, preferably about 0–100 kPa, and most preferably, about 1–20 kPa. In a preferred embodiment, the precipitating solution or diluent solution is delivered through a tube having an outside diameter of substantially about 0.010 inches (about 254 microns) and an inside diameter of substantially about 0.004 to 0.005 inches (about 100 to 127 microns).

In a preferred embodiment, in order to produce a hollow fiber having an approximately 380 micron outside diameter and an approximately 280 micron inside diameter, the polymer dope is delivered to the spinneret at a rate of substantially about 1.0–10 mL/min, more preferably, about 2–5 mL/min, most preferably, about 3–4.5 mL/min, and the precipitating solution is delivered at a rate of at least about 1.0–10 mL/min, more preferably, about 2–5 mL/min, and most preferably, about 2–3 mL/min. The spinneret is oriented in a manner such that fiber production is driven by fluid flow and by removal from the spinneret by gravity effects. Preferably, the fiber emerges from the spinneret and is pulled by gravity and the take-up speed in a nearly vertical direction downwards.

In order to provide satisfactory fibers in the practice of the invention, laminar fluid flow should be maintained both within the spinneret head for the polymeric solution and the precipitating solution which interact to precipitate the formed fiber. If turbulent flow is present in the spinneret head, especially within the channels which convey the polymeric dope, gas pockets may develop and ultimately form large voids in the spun fiber. Turbulent flow within the spun fluids may also result in voids within the fiber.

It is helpful to visualize the spinneret dimensions by resort to ratios of the annular orifice for passage of the polymeric dope and the coaxial tubular orifice for passage of the diluent or precipitating solution. One helpful ratio is the ratio of the cross-sectional area of the annular orifice to tubular orifice. Preferably, the ratio is greater than about 1:1, more preferably, the ratio is about 3:1 to 25:1, and most preferably, the ratio of the annular orifice to tubular orifice cross-sectional area is about 4:1 to 15:1.

Another helpful dimensional ratio is the annular ring thickness to tube inside diameter. Preferably, the ratio is greater than about 1:1, more preferably, the ratio is about 1.5:1 to 7:1, and most preferably, the ratio of the annular ring thickness to tube inside diameter is about 2:1 to 6:1.

A third helpful dimensional ratio is the outside diameter of the annular orifice to tube inside diameter. Preferably, this ratio is greater than about 2:1, more preferably, the ratio is about 3:1 to 10:1, and most preferably, the ratio of the annular outside diameter to tube inside diameter is about 4:1 to 8:1.

As the fiber emerges from the spinneret, it drops in a substantially downward vertical direction over a distance of about 0.1 to 10 m, more preferably, about 0.5 to 2.0 m, and most preferably, about 0.5 to 1.5 m. This allows the precipitating solution to substantially precipitate the polymer in the annular dope solution forming the solid fiber capillary before it is immersed in a quenching solution. Between the spinneret and the quenching bath, the fiber drops through the atmosphere, air, air with a particular relative humidity, an augmented atmosphere, e.g., a mixture of air or air with a particular relative humidity and a gas, an inert gas, or a mixture thereof. Preferably, for ease in processing and to produce a high quality fiber, the fiber drops through air maintained at a temperature of 0° C. to 100° C., more preferably, the air is maintained at a temperature of 5° C. to 50° C. and most preferably at 15° C. to 25° C. Preferably the air is also maintained at a relative humidity of substantially about 10% to 99%, more preferably from substantially about 20% to 80% and most preferably from substantially about 40% to 65%. This gaseous atmosphere may be relatively stagnant, or there can be fluid flow. Preferably, the flow rate is sufficient to allow complete air change over in the spinning environment once every 30 minutes. In one preferred embodiment, the gas flow is about 10 L/min. In an alternative embodiment, the fiber may be dropped directly into the quenching bath.

The fiber is submerged in a tank comprising water and 0–10 wt. % other materials. Again, the water may be tap, deionized water, or the product of a reverse osmosis process. The temperature of the quenching bath is preferably between about 0° to 100° C., more preferably, about 15° C. to 45° C., and most preferably, about 35° C. The water temperature directly affects the performance of the fiber. Lower temperatures can reduce the flux of the resulting fiber. Increasing the quenching bath temperature can increase the flux of the fiber.

The fiber is preferably immersed in the quenching bath for a period of about 0.1 to 10 seconds, preferably about 0.1 to 5 seconds, and most preferably, about 1 second. This residence time permits the full precipitation of the polyimide polymer to form the microporous hollow fiber.

After the quenching bath, the fiber may be further rinsed to remove any remaining solvents. This rinsing may be accomplished in a water bath arrangement. Preferably, the additional rinse is achieved in a water bath having a water temperature of about 0° C.–100° C., more preferably, about 15° C.–45° C., and most preferably, about 35° C. The fiber is then wound on a take-up reel. The take-up reel is preferably rotating at a speed such that the fiber is being wound at about 90–150% of the race at which it is being formed at the spinneret or, in other words, at approximately about 150–230 ft/min (about 45–70 m/min) More preferably, the fiber is being wound at a rate substantially equal to that at which it is being produced. In other words, the fiber is taken up with enough speed (i) to create a fiber of the desired size and (ii) to apply sufficient tension to the fiber such that it will remain taut in the take-up guide unaffected by ambient air currents, i.e. there is no "draft."

The hollow fibers may then be dried by any method appropriate to general manufacturing procedures including but not limited to air, heat, vacuum, or any combination thereof. The hollow fibers may be further processed to form useful articles including hemodialyzer cartridges, hemofilters, blood filters, water filters, etc., having improved performance levels.

For example, at a 300 mL/min flow rate, a clearance rate of at least about 225 mL/min is possible for urea; at least about 200 mL/min for creatinine; and at least about 125 mL/min for Vitamin $B_{12}$. The flux rate possible with the fibers of the present invention is preferably greater than 500 mL/hr/mmHg/m$^2$, more preferably is between 500–1000 mL/hr/mmHg/m$^2$, and most preferably is greater than 1000 mL/hr/mmHg/m$^2$. The sieving coefficient for BSA is preferably less than about 0.01, and most preferably is about 0.0. Sieving coefficients for myoglobulin were between about 0.65 and 1.0. Typical clearance rate data for fibers formed in accordance with the present invention are as follows:

| Flow Rate | Urea | Creatinine | Phosphate | B-12 | Cyto C |
|---|---|---|---|---|---|
| 200 mL/m | 175–200 | 165–200 | 155–195 | 110–130 | 125–185 |
| 300 mL/m | 225–290 | 200–270 | 170–250 | 125–150 | 140–265 |
| 400 mL/m | 250–320 | 215–305 | 195–280 | 125–160 | 150–255 |

EXAMPLES

The following specific examples which contain the best mode, can be used to further illustrate the invention. These examples are merely illustrative of the invention and do not limit its scope.

Example 22

A polymeric dope solution was formed by dissolving 17.5 wt. % of P-84 in dimethylformamide. The material was filtered and then pumped to a tube-in-orifice- spinneret at a rate of 4.50 mL/min and at a temperature of 24° C. Simultaneously, a precipitating solution consisting of 80 wt. % dimethylformamide and 20 wt. % reverse osmosis deionized water was mixed, filtered and delivered to the spinneret at a temperature of 24° C. and a rate of 2.75 mL/min.

The polymeric dope solution was delivered through the outer, annular orifice of the spinneret, which orifice had an outside dimension of about 0.022 to 0.025 inches (about 560 μm) and an inside dimension of about 0.010 inches (about 254 μm). The precipitating solution was delivered through a tube orifice within the annular orifice, which tube orifice had an inside diameter of about 0.005 inches (about 127 μm). The spinneret head was maintained at 24° C. The spinneret discharged the polymeric solution and precipitating solution downward into ambient atmosphere for a distance of about 1.5 meters into a quenching bath maintained at 32° C. Formed fiber material was wound on a take-up reel at a rate of 70 m/min. The fiber was then removed from the take-up wheel, cut, bundled, soaked in a water bath at 32° C. for 10 hours, dried and tested.

Test Data #6

Fiber membranes prepared by the method recited in Example 22 had sieving coefficients of 0.0 for albumin, 0.82 for myoglobin and 1.0 for inulin. These fibers had the surprising advantage of having high sieving coefficients for middle molecules (molecular weights of from about 5,000 daltons to 25,000 daltons) such as $\beta_2$ microglobulins and myoglobins.

| Flow Rate | Urea | Creatinine | Phosphate | B-12 | Cyto C |
|---|---|---|---|---|---|
| 200 mL/m | 179.4 | 164.9 | 156.5 | 125.1 | 129.9 |
| 300 mL/m | 225.0 | 198.5 | 182.6 | 140.2 | 143.0 |
| 400 mL/m | 244.8 | 212.5 | 208.7 | 149.3 | 146.8 |

Example 23

The method for preparing fiber as in Example 22 was repeated using a precipitating solution of 81 wt. % DMF and 19 wt. % deionized water.

Test Data #7

Resultant fiber membranes had sieving coefficients of 0.0 for albumin, 0.79 for myoglobin, and 1.0 for inulin.

| Flow Rate | Urea | Creatinine | Phosphate | B-12 | Cyto C |
|---|---|---|---|---|---|
| 200 mL/m | 188.1 | 178.3 | 166.7 | 119.8 | 156.9 |
| 300 mL/m | 249.6 | 223.4 | 212.5 | 136.6 | 178.7 |
| 400 mL/m | 281.5 | 246.7 | 233.5 | 139.6 | 184.0 |

Example 24

The method employed in Example 22 was repeated using 17.0 wt. % of the P-84 polyimide polymer and 83 wt. % DMF. The precipitating solution comprised 81 wt. % DMF and 19.0 wt. % deionized water. Sieving coefficients were similar to the Test Data obtained for Examples 22 and 23 above for albumin and inulin with a sieving coefficient of 0.77 for myoglobulin.

Test Data #8

| Blood Fl. | Urea | Creatinine | Phosphate | B-12 | Cytochrome C |
|---|---|---|---|---|---|
| 200 mL/m | 190.7 | 178.4 | 166.7 | 124.8 | 162.9 |
| 300 mL/m | 255.2 | 232.45 | 228.0 | 141.5 | 185.7 |
| 400 mL/m | 287.3 | 256.9 | 240.0 | 145.3 | 188.8 |

Example 25

Fibers for use in a water filter were manufactured in the following manner. A polymeric dope solution was formed by dissolving 19.0 wt. % of Matrimid 5218 in 81.0 wt. % DMF. The material was filtered and then pumped to a tube-in-orifice spinneret at a rate of 2.9 mL/min at a temperature of 23° C. Simultaneously, a precipitating solution consisting of 85.5 wt. % DMF and 14.5 wt. % water was mixed, filtered and delivered to the spinneret at a temperature of 23° C. and a rate of 3.0 mL/min.

The polymeric dope solution was delivered through the outer, annular orifice of the spinneret having an outside diameter of 940 μm and an inside diameter of 254 μm. The precipitating solution was delivered through a tube orifice within the annular orifice having an inside diameter of about 127 μm. The spinneret head was maintained at about 23° C. The spinneret discharged the column of polymeric solution and precipitating solution downward for a distance of about 0.81 m into a quenching water bath maintained at a temperature of 35° C. The fiber was wound on a take-up reel at a rate of about 45 m/min. Cut bundles were soaked in a 46° C. water bath for 16 hours. Fiber bundles were dried and tested. Based on a 0.05 m² test mat, at 5 psi, water permeability was calculated to be 500 mL/hr/mmHg/m².

Example 26

Fibers for use in a plasma filter were manufactured in the following manner. The method for preparing fiber as in Example 25 was repeated using a polymeric dope solution consisting of 16.75% P-84 polymer and 83.25 wt. % DMF. The precipitating solution included 85.5 wt. % DMF and 14.5 wt. % deionized water. Fibers had a sieving coefficient of 0.65 using a 0.1% solution of fluorescein isothiocyanate dextran (Sigma), a molecular weight marker of approximately 500,000 Daltons. Water permeability was in excess of 900 mL/hr/mmHg/m².

Example 27

Fibers for use in a water filter were manufactured in the following manner. A polymeric dope solution was formed by dissolving 16.75 wt. % P-84 polymer in 83.25 wt. % DMF. The material was filtered and then pumped to a tube-in-orifice spinneret at a rate of 4.5 mL/min at a temperature of 23° C. Simultaneously, a precipitating solution consisting of 85.5 wt. % DMF and 14.5 wt. % water was mixed, filtered and delivered to the spinneret at a temperature of 23° C. and a rate of 3.0 mL/min.

Fibers were further processed in accordance with the method of Example b 25. A water filter (1.5 m² of fiber) containing the fibers manufactured using the above formulation was tested for water permeability. At 8.6 psi, filters had a water permeability of 1020 mL/hr/mmHg/m². At 10.0 psi, filters had a water permeability of 1320 mL/hr/mmHg/m².

Example 28

Fibers for use in water filters were prepared in the following manner. A polymeric dope solution was formed by dissolving 15.2 wt. % P-84 polyimide polymer in 79.80 wt. % DMF and 5.0 wt. % glacial acetic acid. The material was filtered and pumped to a tube-in-orifice spinneret at a rate of 4.1 mL/min. A precipitating solution comprised of 50 wt. % DMF and 50 wt. % glacial acetic acid was mixed, filtered and delivered to the spinneret at a rate of 4.5 mL/min.

The polymeric dope solution was delivered through the outer, annular orifice of the spinneret having an outside dimension of about 0.029 inches (737 µm) and an inside dimension of about 0.01 inches (about 254 µm). The precipitating solution was delivered through a tube orifice within the annular orifice having an inside diameter of about 0.005 inches (about 127 µm). Precipitated fiber was quenched in a reverse osmosis water bath and taken up at a rate of 49 m/min.

Water Permeability

All fibers produced in the Examples 22–28 above were evaluated for water permeability (flux) in the following manner. Water was passed through the lumens of potted test fibers with the filtering unit in a horizontal position. The ultrafiltrate port on the inlet side of the unit was plugged. Pressure monitors were placed at all inlet and outlet ports. With flow through the unit, backpressure was applied to the fiber outlet side of the unit to increase ultrafiltrate flow across the fibers. Three data points were taken at 10%, 50%, and 80–100% ultrafiltrate flow and transmembrane pressure (TMP) was calculated. Ultrafiltrate flow was plotted against TMP and the slope of this curve was used to determine flux or water permeability. As noted above, all of the above fibers for use as water filters, hemofilters and dialyzers had water permeabilities in excess of 500 mL/hr/mmHg/m².

Endotoxin Tests

Filtering units prepared substantially in accordance with Examples 22–28 were tested with two liters of a bicarbonate solution containing a 15 EU/ml endotoxin challenge at high flow rates. No endotoxin was passed even after repeated recirculations.

The endotoxin solution was prepared by adding 0.25 ml of endotoxin (Control standard endotoxin, lot #47, 25 mcg/ml endotoxin, available from Associates of Cape Cod, Mass.) to a bicarbonate solution. The bicarbonate solution was made from an in-house preparation of bicarbonate concentrate powder by mixing the powder with sufficient reverse osmosis water to make 2½ gallons. The limulus amebocyte lysate used for the assay had a sensitivity of 0.06 EU/ml.

The bicarbonate solution tested negative for endotoxin. The solution with the added endotoxin tested positive at the ninth fold dilution tube (256×) giving an endotoxin concentration between 15.4 and 30.7.

Test solution was recirculated from a two liter flask. The test solution was pumped through the filtering unit by at Sarns portable pump code 5M6002 serial #3397.

Test Data #9
Endotoxin testing

|  | Endotoxin Levels Observed | |
| --- | --- | --- |
| Time | After Filtering | Before Filtering |
| 1 minute | none (<0.06 EUml) | 15.4 |
| 5 minutes | none | 0.96 EU/ml |
| 30 minutes | none | none |
| 60 minutes | none | none |

Test Data #10
Endotoxin testing

|  | Endotoxin Levels Observed | |
| --- | --- | --- |
| Time | After Filtering | Before Filtering |
| 1 minute | none (<0.06 EU/ml) | |
| 5 minutes | none | 0.49 EU/ml |
| 30 minutes | none | none |
| 60 minutes | none | none |
| 120 minutes | none | none |

Although the description of the preferred embodiment and best mode has been presented, it is contemplated that various charges, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

We claim:

1. An asymmetrical, microporous, hollow fiber comprising a mixture of polysulfone and polyvinyl pyrrolidone which is a product of a process comprising the steps of:
    (a) passing, through an outer annular orifice of a tube-in-orifice spinneret, a polymeric solution comprising about 11 to 25 wt-% of a hydrophobic, polysulfone polymer and about 0.1 to 5 wt-% of a polyvinylpyrrolidone polymer dissolved in an aprotic solvent and having a viscosity of about 700 to 3500 cP to form an annular liquid, wherein the tube-in-orifice spinneret has an inner tube, said inner tube and said outer annular orifice each having a cross-sectional area such that the ratio of the respective cross-sectional areas of the outer annular orifice to the inner tube is about 5:1 or greater;
    (b) simultaneously passing, through the inner tube of the tube-in-orifice spinneret, into the center of the annular liquid, a precipitating solution comprising:
        (i) about 30 to 90 wt-% of a lower alcohol;
        (ii) about 10 to 35 wt-% of water;
    (c) passing the annular liquid and the precipitating solution in the center of the annular liquid through a vertical drop of at least about 1 meter in an atmosphere or an augmented atmosphere, wherein the precipitating solution interacts with the polymeric solution within the annular liquid to form an annular polymer precipitate;
    (d) quenching the annular polymer precipitate in a bath to form a hollow fiber, wherein the spinneret and the quenching bath are separated by a vertical distance of at least about 1 meter; and
    (e) taking up the fiber at a rate of about 90 to 150% of the rate at which it is formed.

2. The product of claim 1 wherein the polysulfone comprises a polymer of the formula:

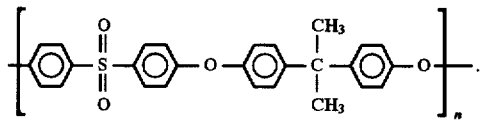

3. The product of claim 1 wherein the polysulfone comprises a polyethersulfone.

4. The product of claim 1 wherein the polysulfone comprises a polyarylsulfone.

5. The product of claim 1 wherein the polyvinylpyrrolidone polymer has a K-value of about 80 to 93.

6. The product of claim 1 wherein the aprotic solvent is selected from the group consisting of dimethylformamide, dimethylacetamide, dimethylsulfoxide, N-methylpyrrolidone and mixtures thereof.

7. The product of claim 6 wherein the aprotic solvent comprises dimethylacetamide.

8. The product of claim 1 wherein the lower alcohol is selected from the group consisting of methanol, ethanol, propanol, isopropanol and mixtures thereof.

9. The product of claim 1 wherein the quenching bath is maintained at about 15° to 45° C.

10. The product of claim 1 wherein the passing step is in a augmented atmosphere selected from the group consisting of humidified air, nitrogen, argon and mixtures thereof.

11. The product of claim 10 comprising circulating the augmented atmosphere.

12. The product of claim 10 wherein the augmented atmosphere comprises humidified air with a relative humidity of about 20 to 100%.

13. The product of claim 1 wherein the spinneret and quenching bath are separated by about 1 to 3 m.

14. The product of claim 1 which further comprises washing the hollow fiber after quenching.

15. The product of claim 1 wherein the hollow fibers are formed at a rate of at least about 30 m/min.

16. The product of claim 1 wherein the polymeric solution is delivered to the spinneret at a rate of at least about 0.1 mL/min and a temperature of about 5° to 85° C.

17. The product of claim 1 wherein the precipitating solution is delivered to the spinneret at a rate of at least about 0.1 mL/min and a temperature of about −10° to 85° C.

18. The product of claim 1 wherein the outer annular orifice of the spinneret has a outside diameter of about 0.015 to 0.025 inches and an inside diameter of about 0.005 to 0.010 inches.

19. The product of claim 1 wherein the tube of the spinneret has an inside diameter of about 0.001 to 0.010 inches.

20. A process for the manufacture of an improved microporous hollow fiber membrane having improved flux and rewetting characteristics, the process comprising:
    (a) passing, through an outer annular orifice of a tube-in-orifice spinneret, a polymeric solution comprising about 5 to 25 wt-% of a hydrophobic polysulfone polymer and about 1 to 25 wt-% of a hydrophilic polyvinylpyrrolidone polymer dissolved in an aprotic solvent and having a viscosity of about 100 to 10,000 cP to form an annular liquid, wherein the tube-in-orifice spinneret has an inner tube, said inner tube and said outer annular orifice each having a cross-sectional area such that the ratio of the respective cross-sectional areas of the outer annular orifice to the inner tube is about 5:1 or greater;
    (b) simultaneously passing, through the inner tube of the spinneret, into the center of the annular liquid a precipitating solution comprising:
        (i) about 0.1 to 100 wt-% of an organic solvent; and
        (ii) about 0.1 to 100 wt-% of water as a nonsolvent;
    (c) passing the annular liquid and the precipitating solution in the center of the annular liquid through a vertical drop of at least about 1 meter in an atmosphere or an augmented atmosphere, wherein the precipitating solution interacts with the polymeric solution within the annular liquid to form an annular polymer precipitate;
    (d) quenching the annular polymer precipitate in a quenching bath comprising from about 0.001 to 10 wt-% of a low molecular weight surfactant to form a hollow fiber, wherein the spinneret and the quenching bath are separated by a vertical distance of at least about 1 meter; and
    (e) taking up the fiber at a rate of about 90 to 150% of the rate at which it is formed;
wherein the fiber has a flux of at least $5 \times 10^{-5}$ mL/min/cm$^2$/mmHg and rewets by maintaining said flux for at least five use and drying cycles.

21. The process of claim 20 wherein the polysulfone polymer comprises a polymer of the formula:

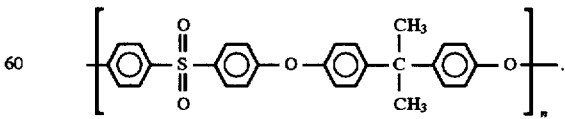

22. The process of claim 20 wherein the polysulfone polymer comprises a polyethersulfone polymer.

23. The process of claim 20 wherein the polysulfone polymer comprises a polyarylsulfone polymer.

24. The process of claim 20 wherein the aprotic solvent is selected from the group consisting of dimethylformamide (DMF), dimethylsulfoxide (DMSO), dimethylacetamide (DMA), N-methylpyrrolidone and mixtures thereof.

25. The process of claim 20 wherein the organic solvent is selected from the group consisting of dimethylformamide (DMF), dimethylacetamide (DMA), isopropanol and mixtures thereof.

26. The process of claim 20 wherein the precipitating solution comprises 40 wt. % dimethylacetamide, 40 wt. % isopropanol, and 20 wt. % water.

27. The process of claim 20 wherein the precipitating solution comprises 40 wt. % dimethylformamide, 40 wt. % isopropanol, and 20 wt. % water.

28. The process of claim 20 wherein the precipitating solution comprises from about 90–98 wt. % isopropanol and 10–2 wt. % water.

29. The process of claim 20 wherein the surfactant is selected from the group consisting of a nonionic, anionic, amphoteric surfactant and mixtures thereof.

30. The process of claim 29 wherein the surfactant is selected from the group consisting of an aromatic hydrophobic based acid ester, an alkoxylated alkylamine, a lauroampho-diacetate/sodium trideceth sulfate, and mixtures thereof.

31. The process of claim 30 wherein the surfactant comprises an alkoxylated fatty amine.

32. The process of claim 31 wherein the alkoxylated fatty amine surfactant is selected from the group consisting of an alkoxylated cocoamine and an ethoxylated (2–15 EO) cocoamine.

33. The process of claim 20 wherein the surfactant is selected from the group consisting of an aromatic hydrophobic based acid ester, an alkoxylated alkylamine, a lauroampho-diacetate/sodium trideceth sulfate, and mixtures thereof.

34. The process of claim 20 wherein the surfactant comprises an alkoxylated fatty amine.

35. The process of claim 20 wherein the alkoxylated fatty amine surfactant is selected from the group consisting of an alkoxylated cocoamine and an ethoxylated (2–15 EO) cocoamine.

36. The process of claim 20 further comprising cutting and forming the fibers into bundles.

37. The product made in accordance with the process of claim 20.

38. A process for the manufacture of an improved microporous hollow fiber membrane having improved flux and rewetting characteristics, the process comprising:

(a) passing, through an outer annular orifice of a tube-in-orifice spinneret, a polymeric solution comprising about 5 to 25 wt-% of a hydrophobic polysulfone polymer and about 1 to 25 wt-% of a hydrophilic polyvinylpyrrolidone polymer dissolved in an aprotic solvent and having a viscosity of about 100 to 10,000 cP to form an annular liquid, wherein the tube-in-orifice spinneret has an inner tube, said inner tube and said outer annular orifice each having a cross-sectional area such that the ratio of the respective cross-sectional areas of the outer annular orifice to the inner tube is about 5:1 or greater;

(b) simultaneously passing, through the inner tube of the spinneret, into the center of the annular liquid a precipitating solution comprising:

(i) about 0.1 to 100 wt-% of an organic solvent; and
(ii) about 0.1 to 100 wt-% of water as a nonsolvent;

(c) passing the annular liquid and the precipitating solution in the center of the annular liquid through a vertical drop of at least about 1 meter in an atmosphere or an augmented atmosphere, wherein the precipitating solution interacts with the polymeric solution within the annular liquid to form an annular polymer precipitate;

(d) quenching the annular polymer precipitate in a quenching bath to form hollow fibers, wherein the spinneret and the quenching bath are separated by a vertical distance of at least about 1 meter;

(e) taking up the fibers at a rate of about 90 to 150% of the rate at which they are formed;

(f) cutting and forming the fibers into bundles; and (g) contacting the bundles with a solution comprising from about 0.001 to 10 wt-% of a low molecular weight surfactant;

wherein the resultant fibers have a flux of at least $5\times10^{-5}$ mL/min/cm$^2$/mmHg, contain from about $1.0\times10^{-5}$ g to about 0.1 g of surfactant per gram of fibers and rewet by maintaining said flux for at least five use and drying cycles.

39. The process of claim 38 wherein the bundles are soaked in the surfactant containing solution for at least about 10 seconds.

40. The process of claim 38 wherein the bundles are soaked in the surfactant containing solution for about 18 to 24 hours.

41. The process of claim 38 wherein the surfactant containing solution is maintained at about 0° C. to 50° C.

42. The process of claim 41 wherein the bundles are soaked in the surfactant containing solution for at least about 10 seconds.

43. The process of claim 41 wherein the bundles are soaked in the surfactant containing solution for about 18 to 24 hours.

44. The process of claim 41 wherein the organic solvent is selected from the group consisting of dimethylformamide (DMF), dimethylacetamide (DMA), isopropanol and mixtures thereof.

45. The process of claim 41 wherein the precipitating solution comprises 40 wt. % dimethylacetamide, 40 wt. % isopropanol, and 20 wt. % water.

46. The process of claim 41 wherein the precipitating solution comprises 40 wt. % dimethylformamide, 40 wt. % isopropanol, and 20 wt. % water.

47. The process of claim 41 wherein the precipitating solution comprises from about 90–98 wt. % isopropanol and 10–2 % water.

48. The process of claim 38 wherein the organic solvent is selected from the group consisting of dimethylformamide (DMF), dimethylacetamide (DMA), isopropanol and mixtures thereof.

49. The process of claim 38 wherein the precipitating solution comprises 40 wt. % dimethylacetamide, 40 wt. % isopropanol, and 20 wt. % water.

50. The process of claim 38 wherein the precipitating solution comprises 40 wt. % dimethylformamide, 40 wt. % isopropanol, and 20 wt. % water.

51. The process of claim 38 wherein the precipitating solution comprises from about 90–98 wt. % isopropanol and 10–2 wt. % water.

52. The product made in accordance with the process of claim 38.

53. A process for the manufacture of an improved microporous hollow fiber membrane having improved flux and rewetting characteristics, the process comprising:

(a) passing, through an outer annular orifice of a tube-in-orifice spinneret, a polymeric solution comprising about 5 to 25 wt-% of a hydrophobic polysulfone polymer, from about 0.001 to about 10 wt-% of a low molecular weight surfactant and about 1 to 25 wt-% of a hydrophilic polyvinylpyrrolidone polymer dissolved in an aprotic solvent, and having a viscosity of about 100 to 10,000 cP to form an annular liquid, wherein the tube-in-orifice spinneret has an inner tube, said inner tube and said outer annular orifice each having a cross-sectional area such that the ratio of the respective cross-sectional areas of the outer annular orifice to the inner tube is about 5:1 or greater;

(b) simultaneously passing, through the inner tube of the spinneret, into the center of the annular liquid a precipitating solution comprising:
(i) about 0.1 to 100 wt-% of an organic solvent; and
(ii) about 0.1 to 100 wt-% of water as a nonsolvent (c) passing the annular liquid and the precipitating solution in the center of the annular liquid through a vertical drop of at least about 1 meter in an atmosphere or an augmented atmosphere, wherein the precipitating solution interacts with the polymeric solution within the annular liquid to form an annular polymer precipitate;

(d) quenching the annular polymer precipitate in a bath to form a hollow fiber; and (e) taking up the fiber at a rate of about 90 to 150% of the rate at which it is formed;

wherein the fiber has a flux of at least about $5 \times 10^{-5}$ mL/min/cm$^2$/mmHg and rewets by maintaining said flux for at least five use and drying cycles.

54. The process of claim 53 wherein the polysulfone polymer comprises a polymer of the formula:

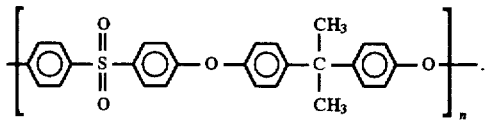

55. The process of claim 53 wherein the polysulfone polymer comprises a polyethersulfone polymer.

56. The process of claim 53 wherein the polysulfone polymer comprises a polyarylsulfone polymer.

57. The process of claim 53 wherein the aprotic solvent is selected from the group consisting of DMF, DMA, DMSO, N-methylpyrrolidone and mixtures thereof.

58. The process of claim 53 wherein the organic solvent is selected from the group consisting of dimethylformamide (DMF), dimethylacetamide (DMA), isopropanol and mixtures thereof.

59. The process of claim 53 wherein the precipitating solution comprises 40 wt. % dimethylacetamide, 40 wt. % isopropanol, and 20 wt. % water.

60. The process of claim 53 wherein the precipitating solution comprises 40 wt. % dimethylformamide, 40 wt. % isopropanol, and 20 wt % water.

61. The process of claim 53 wherein the precipitating solution comprises from about 90–98 wt. % isopropanol and 10–2 wt. % water.

62. The process of claim 53 wherein the surfactant is selected from the group consisting of a nonionic, anionic, or amphoteric surfactant and mixtures thereof.

63. The process of claim 62 wherein the surfactant is selected from the group consisting of an aromatic hydrophobic based acid ester, an alkoxylated alkylamine, a lauroampho-diacetate/sodium trideceth sulfate and mixtures thereof.

64. The process of claim 63 wherein the surfactant comprises an alkoxylated fatty amine.

65. The process of claim 64 wherein the alkoxylated fatty amine surfactant is selected from the group consisting of an alkoxylated cocoamine and an ethoxylated (2–15 EO) cocoamine.

66. The process of claim 53 wherein the surfactant is selected from the group consisting of an aromatic hydrophobic based acid ester, an alkoxylated alkylamine, a lauroampho-diacetate/sodium trideceth sulfate, and mixtures thereof.

67. The process of claim 53 wherein the surfactant comprises an alkoxylated fatty amine.

68. The process of claim 53 wherein the alkoxylated fatty amine surfactant is selected from the group consisting of an alkoxylated cocoamine and an ethoxylated (2–15 EO) cocoamine.

69. The product made in accordance with the process of claim 53.

70. An improved process for the manufacture of asymmetrical, microporous, hollow fibers, the process comprising:

(a) passing, through an outer annular orifice of a tube-in-orifice spinneret, a polymeric solution comprising about 11 to 25 wt-% of a hydrophobic, polysulfone polymer and about 0.1 to 5 wt-% of a polyvinylpyrrolidone polymer dissolved in an aprotic solvent and having a viscosity of about 700 to 3500 cP to form an annular liquid, wherein the tube-in-orifice spinneret has an inner tube, said inner tube and said outer annular orifice each having a cross-sectional area such that the ratio of the respective cross-sectional areas of the outer annular orifice to the inner tube is about 5:1 or greater;

(b) simultaneously passing, through the inner tube of the tube-in-orifice spinneret, into the center of the annular liquid, a precipitating solution comprising:
(i) about 30 to 90 wt-% of a lower alcohol; and
(ii) about 10 to 35 wt-% of water;

(c) passing the annular liquid and the precipitating solution in the center of the annular liquid through a vertical drop of at least about 1 meter in an atmosphere or an augmented atmosphere, wherein the precipitating solution interacts with the polymeric solution within the annular liquid to form an annular polymer precipitate;

(d) quenching the annular polymer precipitate in a quenching bath to form hollow fibers, wherein the spinneret and the quenching bath are separated by a vertical distance of at least about 1 meter; and (e) taking up the fibers at a rate of about 90 to about 150% of the rate at which they are formed.

71. The process of claim 70 wherein the polysulfone comprises a polymer of the formula:

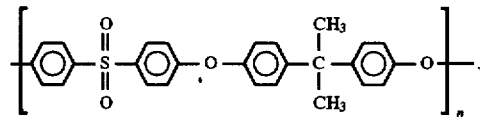

72. The process of claim 70 wherein the polysulfone comprises a polyethersulfone.

73. The process of claim 70 wherein the polysulfone comprises a polyarylsulfone.

74. The process of claim 70 wherein the polyvinylpyrrolidone polymer has a K-value of about 80 to 93.

75. The process of claim 70 wherein the aprotic solvent is selected from the group consisting of dimethylformamide, dimethylacetamide, dimethylsulfoxide, N-methylpyrrolidone and mixtures thereof.

76. The process of claim 75 wherein the aprotic solvent comprises dimethylacetamide.

77. The process of claim 70 wherein the lower alcohol is selected from the group consisting of methanol, ethanol, propanol, isopropanol and mixtures thereof.

78. The process of claim 70 wherein the quenching bath is maintained at about 15° to 45° C.

79. The process of claim 70 wherein the passing step is in a augmented atmosphere selected from the group consisting of humidified air, nitrogen, argon and mixtures thereof.

80. The process of claim 79 comprising circulating the augmented atmosphere.

81. The process of claim 79 wherein the augmented atmosphere comprises humidified air with a relative humidity of about 20 to 100%.

82. The process of claim 70 wherein the spinneret and quenching bath are separated by about 1 to 3 m.

83. The process of claim 70 which further comprises washing the hollow fibers after quenching.

84. The process of claim 70 wherein the hollow fiber are formed at a rate of at least about 30 m/min.

85. The process of claim 70 wherein the polymeric solution is delivered to the spinneret at a rate of at least about 0.1 mL/min and a temperature of about 5° to 85° C.

86. The process of claim 70 wherein the precipitating solution is delivered to the spinneret at a rate of at least about 0.1 mL/min and a temperature of about −10° to 85° C.

87. The process of claim 70 wherein the outer annular orifice of the spinneret has a outside diameter of about 0.015 to 0.045 inches and an inside diameter of about 0.005 to 0.010 inches.

88. The process of claim 70 wherein the tube of the spinneret has an inside diameter of about 0.001 to 0.010 inches.

89. An asymmetrical, microporous, hollow fiber membrane produced according to the process of claim 70 wherein said fibers exhibit sufficient strength to withstand take-up rates of about 75 m/min or greater.

90. An improved process for the manufacture of asymmetrical, microporous, hollow fibers, the process comprising:

(a) passing, through an outer annular orifice of a tube-in-orifice spinneret, a polymeric solution comprising about 15 wt-% of a hydrophobic, polysulfone polymer and about 3 wt-% of a polyvinylpyrrolidone polymer dissolved in an aprotic solvent and having a viscosity of about 1500 cP to form an annular liquid, wherein the tube-in-orifice spinneret has an inner tube, said inner tube and said outer annular orifice each having a cross-sectional area such that the ratio of the respective cross-sectional areas of the outer annular surface to that of the inner tube is about 10:1 or greater;

(b) simultaneously passing, through the inner tube of the tube-in-orifice spinneret, into the center of the annular liquid, a precipitating solution comprising:
  (i) about 80 wt-% of isopropyl alcohol; and
  (ii) about 20 wt-% of water;

(c) passing the annular liquid and the precipitating solution in the center of the annular liquid through a vertical drop of at least about 1.5 meters in an atmosphere or an augmented atmosphere maintained at about 20° C., wherein the precipitating solution interacts with the polymeric solution within the annular liquid to form an annular polymer precipitate;

(d) quenching the annular polymer precipitate in a quenching bath to form hollow fibers, wherein the spinneret and quenching bath are separated by a vertical distance of about 1.5 m; and (e) taking up the fiber at a rate substantially equal to the rate at which they are formed.

* * * * *